US010987235B2

(12) United States Patent
Eubanks et al.

(10) Patent No.: US 10,987,235 B2
(45) Date of Patent: Apr. 27, 2021

(54) SYSTEMS, DEVICES, AND METHODS FOR MARKING AND/OR REINFORCING FENESTRATIONS IN PROSTHETIC IMPLANTS

(71) Applicant: Aortica Corporation, Bellevue, WA (US)

(72) Inventors: Shannon E. Eubanks, Woodinville, WA (US); Edward Wulfman, Woodinville, WA (US); Jay Miazga, Langley, WA (US); Daniel Piha, Bellevue, WA (US)

(73) Assignee: Aortica Corporation, Sunrise, FL (US)

( * ) Notice: Subject to any disclaimer, the term of this patent is extended or adjusted under 35 U.S.C. 154(b) by 10 days.

(21) Appl. No.: 16/203,873

(22) Filed: Nov. 29, 2018

(65) Prior Publication Data

US 2019/0328556 A1 Oct. 31, 2019

Related U.S. Application Data

(63) Continuation of application No. PCT/US2017/037157, filed on Jun. 13, 2017.
(Continued)

(51) Int. Cl.
*A61F 2/856* (2013.01)
*A61F 2/06* (2013.01)
*A61F 2/07* (2013.01)

(52) U.S. Cl.
CPC ........... *A61F 2/856* (2013.01); *A61F 2/06* (2013.01); *A61F 2/07* (2013.01); *A61F 2002/061* (2013.01); *A61F 2250/0098* (2013.01)

(58) Field of Classification Search
CPC .... A61F 2/856; A61F 2/06; A61F 2/07; A61F 2002/061; A61F 2250/0098; A61F 2/0811;
(Continued)

(56) References Cited

U.S. PATENT DOCUMENTS 5,123,917 A 6/1992 Lee
5,370,692 A 12/1994 Fink et al.
(Continued)

FOREIGN PATENT DOCUMENTS

CN 104240220 A 12/2014
EP 2471498 A1 7/2012
(Continued)

OTHER PUBLICATIONS

International Search Report and Written Opinion dated Aug. 21, 2017 for International Application No. PCT/US2017/037157, 12 pages.
(Continued)

*Primary Examiner* — Alvin J Stewart
(74) *Attorney, Agent, or Firm* — Foley Hoag LLP

(57) ABSTRACT

Devices, systems, and methods for marking and/or reinforcing fenestrations in grafts are disclosed herein. In some embodiments, a radiopaque marker for a graft is provided. The marker can be secured to the graft in the area near a fenestration such that the marker is visible via radiographic imaging. The radiopaque marker can be in the form of a radiopaque thread, a radiopaque bead, a radiopaque additive, or a radiopaque adhesive. In some embodiments, the radiopaque marker is in the form of a circular disc shaped and sized to surround a fenestration, the circular disc being formed of a radiopaque material. The radiopaque marker can be configured to or can be attached to a reinforcement member configured to reinforce a fenestration such that one
(Continued)

or more edges of the fenestration are protected and/or to aid in engagement with and sealing to a mating stent.

17 Claims, 21 Drawing Sheets

Related U.S. Application Data

(60) Provisional application No. 62/349,287, filed on Jun. 13, 2016.

(58) Field of Classification Search
CPC ............ A61B 17/11; A61B 2017/1103; A61B 2017/1107; A61B 17/1114
See application file for complete search history.

(56) References Cited

U.S. PATENT DOCUMENTS

| | | | |
|---|---|---|---|
| 5,507,769 A | 4/1996 | Marin et al. | |
| 5,607,444 A * | 3/1997 | Lam | A61F 2/90 |
| | | | 604/104 |
| 5,755,769 A | 5/1998 | Richard et al. | |
| 5,984,955 A * | 11/1999 | Wisselink | A61F 2/07 |
| | | | 623/1.35 |
| 6,030,414 A * | 2/2000 | Taheri | A61F 2/07 |
| | | | 623/1.1 |
| 6,036,702 A * | 3/2000 | Bachinski | A61B 17/11 |
| | | | 606/153 |
| 6,059,824 A * | 5/2000 | Taheri | A61F 2/856 |
| | | | 623/1.15 |
| 6,171,334 B1 | 1/2001 | Cox | |
| 6,280,464 B1 | 8/2001 | Hayashi | |
| 6,395,018 B1 * | 5/2002 | Castaneda | A61F 2/07 |
| | | | 623/1.13 |
| 6,524,335 B1 * | 2/2003 | Hartley | A61F 2/07 |
| | | | 623/1.13 |
| 6,616,675 B1 * | 9/2003 | Evard | A61B 1/3137 |
| | | | 606/153 |
| 6,719,768 B1 * | 4/2004 | Cole | A61B 17/0057 |
| | | | 606/153 |
| 7,306,623 B2 * | 12/2007 | Watson | A61F 2/07 |
| | | | 606/153 |
| 7,413,573 B2 * | 8/2008 | Hartley | A61F 2/07 |
| | | | 623/1.13 |
| 7,435,253 B1 | 10/2008 | Hartley et al. | |
| 7,833,266 B2 * | 11/2010 | Gregorich | A61F 2/856 |
| | | | 623/1.35 |
| 8,172,895 B2 | 5/2012 | Anderson et al. | |
| 8,216,298 B2 * | 7/2012 | Wright | A61F 2/07 |
| | | | 623/1.13 |
| 8,236,040 B2 | 8/2012 | Mayberry et al. | |
| 8,249,815 B2 | 8/2012 | Taylor | |
| 8,287,586 B2 * | 10/2012 | Schaeffer | A61F 2/07 |
| | | | 623/1.15 |
| 8,337,547 B2 | 12/2012 | Iancea et al. | |
| 8,359,118 B2 | 1/2013 | Ono et al. | |
| 8,480,725 B2 | 7/2013 | Rasmussen et al. | |
| 8,641,752 B1 | 2/2014 | Holm et al. | |
| 8,808,351 B2 * | 8/2014 | Osborne | A61F 2/07 |
| | | | 623/1.13 |
| 8,897,513 B2 | 11/2014 | Balasubramanian | |
| 8,945,202 B2 * | 2/2015 | Mayberry | A61F 2/90 |
| | | | 623/1.13 |
| 8,958,623 B1 | 2/2015 | Grady et al. | |
| 9,095,421 B2 | 8/2015 | Peterson | |
| 9,101,455 B2 | 8/2015 | Roeder et al. | |
| 9,125,733 B2 * | 9/2015 | Greenberg | A61F 2/856 |
| 9,259,336 B2 * | 2/2016 | Schaeffer | A61F 2/91 |
| 9,305,123 B2 | 4/2016 | Leotta et al. | |
| 9,629,686 B2 | 4/2017 | Van Bibber et al. | |
| 9,629,705 B2 | 4/2017 | Douthitt et al. | |
| 9,694,108 B2 | 7/2017 | Cully et al. | |
| 9,724,187 B2 | 8/2017 | Ivancev et al. | |
| 9,737,394 B2 | 8/2017 | Coghlan et al. | |
| 9,801,741 B1 | 10/2017 | Thapliyal | |
| 9,861,503 B2 | 1/2018 | Barthold et al. | |
| 10,004,616 B2 * | 6/2018 | Chakfe | A61F 2/07 |
| 10,390,931 B2 | 8/2019 | Douthitt et al. | |
| 10,390,932 B2 * | 8/2019 | Lostetter | A61F 2/07 |
| 10,485,684 B2 * | 11/2019 | Marmur | A61F 2/07 |
| 10,603,196 B2 * | 3/2020 | Mayberry | A61F 2/89 |
| 10,653,484 B2 | 5/2020 | Van Bibber et al. | |
| 2002/0042564 A1 * | 4/2002 | Cooper | A61B 8/12 |
| | | | 600/407 |
| 2002/0042622 A1 * | 4/2002 | Vargas | A61B 17/32053 |
| | | | 606/153 |
| 2002/0062133 A1 | 5/2002 | Gilson et al. | |
| 2002/0095205 A1 | 7/2002 | Edwin et al. | |
| 2002/0188344 A1 | 12/2002 | Bolea et al. | |
| 2002/0193872 A1 * | 12/2002 | Trout, III | A61F 2/07 |
| | | | 623/1.34 |
| 2003/0093145 A1 * | 5/2003 | Lawrence-Brown | |
| | | | A61F 2/954 |
| | | | 623/1.21 |
| 2004/0034406 A1 * | 2/2004 | Thramann | A61F 2/07 |
| | | | 623/1.13 |
| 2004/0059406 A1 * | 3/2004 | Cully | A61F 2/07 |
| | | | 623/1.11 |
| 2004/0064081 A1 | 4/2004 | Stanish | |
| 2004/0102866 A1 | 5/2004 | Harris et al. | |
| 2004/0138737 A1 * | 7/2004 | Davidson | A61F 2/958 |
| | | | 623/1.35 |
| 2005/0102021 A1 * | 5/2005 | Osborne | A61F 2/07 |
| | | | 623/1.13 |
| 2005/0131517 A1 * | 6/2005 | Hartley | A61F 2/07 |
| | | | 623/1.13 |
| 2005/0131518 A1 * | 6/2005 | Hartley | A61F 2/856 |
| | | | 623/1.13 |
| 2005/0131523 A1 | 6/2005 | Bashiri et al. | |
| 2005/0137518 A1 * | 6/2005 | Biggs | A61F 2/86 |
| | | | 604/8 |
| 2005/0149166 A1 * | 7/2005 | Schaeffer | A61F 2/915 |
| | | | 623/1.13 |
| 2005/0171598 A1 * | 8/2005 | Schaeffer | A61F 2/954 |
| | | | 623/1.35 |
| 2006/0020319 A1 | 1/2006 | Kim et al. | |
| 2006/0058638 A1 | 3/2006 | Boese et al. | |
| 2006/0116749 A1 * | 6/2006 | Willink | A61M 25/0084 |
| | | | 623/1.11 |
| 2006/0155359 A1 * | 7/2006 | Watson | A61F 2/07 |
| | | | 623/1.13 |
| 2006/0259116 A1 * | 11/2006 | Feld | A61F 2/958 |
| | | | 623/1.11 |
| 2007/0055360 A1 | 3/2007 | Hanson et al. | |
| 2007/0142900 A1 * | 6/2007 | Balaji | A61F 2/90 |
| | | | 623/1.16 |
| 2007/0244547 A1 * | 10/2007 | Greenan | A61F 2/07 |
| | | | 623/1.35 |
| 2007/0293936 A1 | 12/2007 | Dobak | |
| 2007/0293940 A1 * | 12/2007 | Schaeffer | A61F 2/86 |
| | | | 623/1.16 |
| 2008/0091260 A1 | 4/2008 | Pomeranz et al. | |
| 2008/0109066 A1 * | 5/2008 | Quinn | A61F 2/82 |
| | | | 623/1.13 |
| 2008/0147174 A1 * | 6/2008 | Konstantino | A61F 2/91 |
| | | | 623/1.35 |
| 2008/0201007 A1 | 8/2008 | Boyden et al. | |
| 2008/0269867 A1 | 10/2008 | Johnson | |
| 2009/0030502 A1 * | 1/2009 | Sun | A61F 2/07 |
| | | | 623/1.16 |
| 2009/0264990 A1 | 10/2009 | Bruszewski et al. | |
| 2009/0304245 A1 | 12/2009 | Egger et al. | |
| 2010/0004730 A1 | 1/2010 | Benjamin et al. | |
| 2010/0063576 A1 * | 3/2010 | Schaeffer | A61F 2/07 |
| | | | 623/1.13 |
| 2010/0121429 A1 | 5/2010 | Greenan et al. | |
| 2010/0268319 A1 * | 10/2010 | Bruszewski | A61F 2/07 |
| | | | 623/1.13 |
| 2011/0054586 A1 * | 3/2011 | Mayberry | A61F 2/966 |
| | | | 623/1.11 |

(56) References Cited

U.S. PATENT DOCUMENTS

| | | | |
|---|---|---|---|
| 2011/0060446 A1 | 3/2011 | Ono et al. | |
| 2011/0257720 A1 | 10/2011 | Peterson et al. | |
| 2011/0270378 A1 | 11/2011 | Bruszewski et al. | |
| 2011/0295364 A1* | 12/2011 | Konstantino | A61F 2/91 623/1.35 |
| 2012/0035714 A1 | 2/2012 | Ducke et al. | |
| 2012/0046728 A1* | 2/2012 | Huser | A61F 2/07 623/1.13 |
| 2013/0116775 A1* | 5/2013 | Roeder | A61F 2/856 623/1.35 |
| 2013/0123900 A1 | 5/2013 | Eblacas et al. | |
| 2013/0158648 A1 | 6/2013 | Hartley et al. | |
| 2013/0296998 A1* | 11/2013 | Leotta | G09B 23/30 623/1.11 |
| 2013/0338760 A1* | 12/2013 | Aristizabal | A61F 2/954 623/1.23 |
| 2014/0046428 A1 | 2/2014 | Cragg et al. | |
| 2014/0180393 A1* | 6/2014 | Roeder | A61F 2/07 623/1.15 |
| 2014/0277335 A1* | 9/2014 | Greenberg | A61F 2/856 623/1.11 |
| 2014/0350658 A1* | 11/2014 | Benary | A61F 2/856 623/1.15 |
| 2015/0005868 A1* | 1/2015 | Koskas | A61F 2/852 623/1.13 |
| 2015/0073534 A1* | 3/2015 | Roeder | A61F 2/07 623/1.35 |
| 2015/0105849 A1 | 4/2015 | Cohen et al. | |
| 2015/0202067 A1 | 7/2015 | Barrand et al. | |
| 2015/0209163 A1* | 7/2015 | Kelly | A61F 2/07 623/1.11 |
| 2015/0216686 A1 | 8/2015 | Chakfe et al. | |
| 2015/0238121 A1 | 8/2015 | Tu et al. | |
| 2015/0313596 A1* | 11/2015 | Todd | A61B 17/11 606/153 |
| 2016/0022450 A1* | 1/2016 | Hehrlein | A61F 2/844 623/1.34 |
| 2016/0184078 A1 | 6/2016 | Choubey et al. | |
| 2016/0232667 A1 | 8/2016 | Taylor | |
| 2017/0049588 A1* | 2/2017 | Davis | A61F 2/07 |
| 2017/0112642 A1 | 4/2017 | Hartley et al. | |
| 2017/0333133 A1 | 11/2017 | Van Bibber et al. | |
| 2018/0021130 A1* | 1/2018 | Danino | A61F 2/07 623/1.13 |
| 2018/0064529 A1* | 3/2018 | Sibe | A61F 2/954 |
| 2018/0116832 A1* | 5/2018 | Pillai | A61F 2/856 |
| 2018/0153680 A1 | 6/2018 | Greenberg et al. | |
| 2018/0228593 A1 | 8/2018 | Eaton et al. | |
| 2018/0235787 A1 | 8/2018 | Bolduc et al. | |
| 2018/0243076 A1 | 8/2018 | Greenberg et al. | |
| 2019/0069986 A1* | 3/2019 | Lukas | A61F 2/07 |
| 2019/0231571 A1 | 8/2019 | Lostetter | |
| 2019/0247178 A1 | 8/2019 | Arbefeuille | |
| 2019/0247179 A1 | 8/2019 | Lostetter | |
| 2019/0269497 A1 | 9/2019 | Arbefeuille | |
| 2019/0282355 A1* | 9/2019 | Lostetter | A61F 2/07 |
| 2019/0328556 A1* | 10/2019 | Eubanks | A61F 2/856 |
| 2019/0388213 A1 | 12/2019 | Torrance et al. | |
| 2020/0146808 A1 | 5/2020 | Kratzberg et al. | |
| 2020/0246165 A1 | 8/2020 | Arbefeuille et al. | |

FOREIGN PATENT DOCUMENTS

| | | |
|---|---|---|
| EP | 2517672 A1 | 10/2012 |
| EP | 2 606 851 A1 | 6/2013 |
| EP | 2735283 A1 | 5/2014 |
| EP | 2740440 A2 | 6/2014 |
| EP | 2745812 A1 | 6/2014 |
| EP | 2745813 A1 | 6/2014 |
| EP | 2749250 A1 | 7/2014 |
| EP | 2749251 A1 | 7/2014 |
| EP | 3040054 A1 | 7/2016 |
| EP | 3078349 A1 | 10/2016 |
| EP | 3272319 A1 | 1/2018 |
| FR | 2932979 A1 | 1/2010 |
| JP | 2004-529735 A | 9/2004 |
| JP | 2006-500107 A | 1/2006 |
| JP | 2008-526440 A | 7/2008 |
| JP | 2015-527156 A | 9/2015 |
| WO | WO-97/03624 A1 | 2/1997 |
| WO | WO-97/48350 A1 | 12/1997 |
| WO | WO-01/60285 A1 | 8/2001 |
| WO | WO-02/29758 A2 | 4/2002 |
| WO | WO-02/083038 A2 | 10/2002 |
| WO | WO-2005/034809 A1 | 4/2005 |
| WO | WO 2005/034810 A1 | 4/2005 |
| WO | WO-2006/037086 A1 | 4/2006 |
| WO | WO-2007045000 A2 | 4/2007 |
| WO | WO-2008/124222 A1 | 10/2008 |
| WO | WO-2009/148594 A1 | 12/2009 |
| WO | WO 2010/024867 A1 | 3/2010 |
| WO | WO 2010/024880 A1 | 3/2010 |
| WO | WO 2010/030370 A1 | 3/2010 |
| WO | WO 2010/127040 A1 | 11/2010 |
| WO | WO-2012/116368 A2 | 8/2012 |
| WO | WO-2012/145823 A1 | 11/2012 |
| WO | WO-2013066880 A1 | 5/2013 |
| WO | WO 03/099108 A2 | 12/2013 |
| WO | WO-2014/053616 A1 | 4/2014 |
| WO | WO-2015/070792 A1 | 5/2015 |
| WO | WO 2016/098113 A1 | 6/2016 |
| WO | WO 2017/007947 A1 | 1/2017 |
| WO | WO 2017/218474 A1 | 12/2017 |
| WO | WO 2018/026768 A1 | 2/2018 |

OTHER PUBLICATIONS

International Search Report and Written Opinion dated Jan. 4, 2018 for International Application No. PCT/US2017/044822, 15 pages.
International Search Report and Written Opinion dated Apr. 23, 2019 for International Application No. PCT/US2018/052400, 16 pages.
Notice of Reasons for Rejection dated Jan. 14, 2020 for Japanese Application No. 2018-564736, 11 pages.
Chuter et al., "Fenestrated and Branched Stent-Grafts for thoracoabdominal, Pararenal and Juxtarenal Aortic Aneurysm Repair," Seminars in Vascular Surgery, 20:90-96 (2007).
Chuter et al., "Standardized off-the-shelf components for multi-branched endovascular repair of thoracoabdominal aortic aneurysms," Perspectives in Vascular Surgery and Endovascular Therapy, 23(3):195-201 (2011).
Elkouri et al., "Most patients with abdominal aortic aneurysm are not suitable for endovascular repair using currently approved bifurcated stent-grafts," Vascular and Endovascular Surgery, 38(5):401-412 (2004).
Hazer et al., "A workflow for computational fluid dynamics simulations using patient-specific aortic models," 24th CADFEM Users Meeting 2006, International Congress on FEM Technology with 2006 German ANSYS Conference, Oct. 25, 2006, 9 pages.
Higashiura et al., "Initial experience of branched endovascular graft for abdominal aortic aneurysm with complex anatomy of proximal neck: planning and technical considerations," Jpn J Radiol, 28:66-74 (2010).
Legget et al., "System for quantitative three-dimensional echocardiography of the left ventricle based on a magnetic-field position and orientation system," IEEE Transactions on Biomedical Engineering, 45(4):494-504 (1998).
Leotta et al., "Measurement of abdominal aortic aneurysms with three-dimensional ultrasound imaging: preliminary report," Journal of Vascular Surgery, 33(4):700-707 (2001).
Malina et al., "EVAR and complex anatomy: an update on fenestrated and branched stent grafts," Scandinavian Journal of Surgery, 97:195-204 (2008).
Nordon et al., "Toward an 'off-the-shelf' fenestrated endograft for management of short-necked abdominal aortic aneurysms: an analysis of current graft morphological diversity," J Endovasc Ther., 17:78-85 (2010).

(56) References Cited

OTHER PUBLICATIONS

Oderich et al., "Modified fenestrated stent grafts: device design, modifications, implantation, and current applications," Perspectives in Vascular Surgery and Endovascular Therapy, 21(3):157-167 (2009).
Resch et al., "Incidence and management of complications after branched and fenestrated endographing," Journal of Cardiovascular Surgery, 51(1):105-113 (2010).
Ricotta et al., "Fenestrated and branched stent grafts," Perspective Vascular Surgery and Endovascular Therapy, 20(2):174-187 (2008).
Stratasys, Dimension 1200es 3D modeling printer, Durability Meets Affordability, www.stratasys.com/3d-printers/design-series/performance/dimension-1200es, 2014, 4 pages.
UK Evar Trial Investigators, "Endovascular versus open repair of abdominal aortic aneurysm," New England Journal of Medicine, 362(20):1863-1871 (2010).

* cited by examiner

SYSTEMS, DEVICES, AND METHODS FOR MARKING AND/OR REINFORCING FENESTRATIONS IN PROSTHETIC IMPLANTS

CROSS-REFERENCE TO RELATED APPLICATIONS

This application is a continuation of International Patent Application No. PCT/US2017/037157, filed Jun. 13, 2017 and titled "Systems, Devices, and Methods for Marking and/or Reinforcing Fenestrations in Prosthetic Implants," which claims priority to and the benefit of U.S. Patent Application No. 62/349,287, filed Jun. 13, 2016, entitled "Systems, Devices, and Methods for Marking and/or Reinforcing Fenestrations in Prosthetic Implants," the disclosures of which are incorporated herein by reference in their entirety.

BACKGROUND

Embodiments described herein relate generally to devices, systems and methods for marking and/or reinforcing fenestrations in grafts, such as, for example, aortic stent grafts.

Aneurysms generally involve the abnormal swelling or dilation of a blood vessel such as an artery. The wall of the abnormally dilated blood vessel is typically weakened and susceptible to rupture. For example, an abdominal aortic aneurysm (AAA) is a common type of aneurysm that poses a serious health threat. A common way to treat AAA and other types of aneurysm is to place an endovascular stent graft such that the stent graft spans across and extends beyond the proximal and distal ends of the diseased portion of the vasculature. The stent graft is designed to reline the diseased vasculature, providing an alternate blood conduit that isolates the aneurysm from the high pressure flow of blood, thereby reducing or eliminating the risk of rupture.

Minimally invasive endovascular repair using stent grafts is often preferred to avoid the risks associated with traditional open surgical repair. However, these stent grafts can only be used when the graft can be placed in a stable position without covering major branch vessels. In the cases of juxtarenal aneurysm where the dilation extends up to but does not involve the renal arteries, the proximal portion of the stent graft needs to be secured to the aortic wall above the renal arteries, thereby blocking the openings to the renal arteries. Thus, patients with juxtarenal aneurysms, which represent a significant proportion of abdominal aortic aneurysm cases, are typically excluded from endovascular treatment.

To allow for endovascular repair of a wider range of cases, openings are sometimes created during manufacturing or cut by surgeons in the stent graft body to accommodate specific branch vessel origins, a process known as "fenestration." Thus, for example, in treating juxtarenal aneurysms, the fenestrations or openings of the stent grafts are to be aligned with the renal arteries. Traditionally, the fenestration process involves measurements based on medical images (such as CT scans) of the vessel origins. Longitudinal distances may be measured, and relative angular locations may be estimated from a reference point.

However, these manual measurements may take a substantial amount of time and effort, particularly when multiple branch vessels must be accommodated. For example, in abdominal aortic aneurysms, fenestrations may be required for both left and right renal arteries, the superior mesenteric artery (SMA), and the celiac artery. In addition, approximations of the placement of the branch openings could lead to errors in the placement of the openings compared to the true branch vessel origins. In some cases, openings may be erroneously placed over stent struts. In operating room conditions, surgeons often need to cut fenestrations in the stent body quickly. Additionally, there are challenges associated with cutting graft material both when cut by surgeons in operating room conditions and when fenestrations are created during manufacturing of a graft. Typical graft material is flexible and shifts in response to being pressed on with a cutting tool. Therefore, there is a need for a simple yet accurate and cost-effective way to create fenestrations in stent grafts. Moreover, there is a need for reinforcement of portions of grafts surrounding the fenestrations and for marking the fenestrations such that the fenestrations can be easily located during delivery and/or while the graft is in use.

SUMMARY

Devices, systems, and methods for marking and/or reinforcing fenestrations in grafts are disclosed herein. In some embodiments, a radiopaque marker for a graft is provided. The marker can be secured to the graft in the area near a fenestration such that the marker is visible via radiographic imaging. In some embodiments, the radiopaque marker is in the form of a radiopaque thread, a radiopaque bead, a radiopaque additive, or a radiopaque adhesive. In some embodiments, the radiopaque marker is in the form of a circular disc shaped and sized to surround a fenestration, the circular disc being formed of a radiopaque material. In some embodiments, the radiopaque marker can be configured as or can be attached to a reinforcement member configured to reinforce a fenestration such that one or more edges of the fenestration are protected and/or aid in engagement with and sealing to a mating stent.

DETAILED DESCRIPTION

Figure 1:
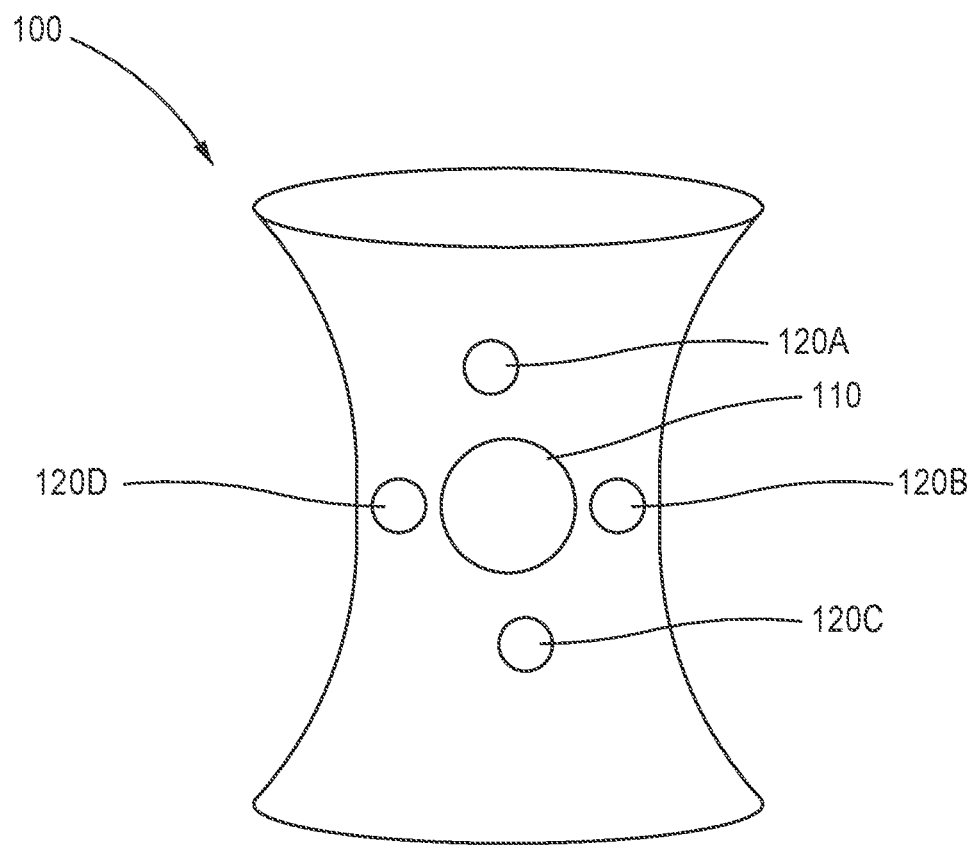
FIG. 1 is a schematic illustration of a template, according to an embodiment.

Devices, systems, and methods for marking and/or reinforcing fenestrations in grafts are disclosed herein. In some embodiments, an apparatus includes a member and at least one radiopaque element. The member can be configured to be secured to a patient-specific prosthetic such that the member surrounds a fenestration defined by the prosthetic. The fenestration can correspond to a location of a branch blood vessel in a portion of a patient's blood vessel. The at least one radiopaque element can be configured to indicate the location of the fenestration via radiographic imaging.

In some embodiments, a radiopaque marker for a graft is provided. The marker can be secured to the graft in the area near a fenestration such that the marker is visible via radiographic imaging. In some embodiments, the radiopaque marker is in the form of and/or includes a radiopaque thread, a radiopaque bead, a radiopaque additive, a radiopaque wire or coil, a radiopaque powder embedded in another substrate, and/or a radiopaque adhesive. In some embodiments, the radiopaque marker is in the form of and/or includes a circular disc shaped and sized to surround a fenestration, the circular disc being formed of a radiopaque material.

In some embodiments, a marker template for a graft is provided. The fenestration template can include one or more openings corresponding to one or more desired marker locations on the graft. The fenestration template can be coupled to the graft such that marker elements can be applied to the graft via the openings. In some embodiments, marker elements can be attached to the fenestration template and transferred to the graft when the fenestration template is coupled to the graft.

In some embodiments, a reinforcing member (also referred to herein as a patch or a grommet) for a graft is provided. The reinforcing member can include radiopaque markers, be formed of a radiopaque material, and/or be embedded with a radiopaque material. The reinforcing member can be configured and applied to the graft such that the fenestration is reinforced and/or protected. For example, the reinforcing member can prevent fraying of the edge of a fenestration of the graft. In some embodiments, the reinforcing member can aid in engagement and sealing between the graft and another mating stent. In some embodiments, the reinforcement member can be formed as a patch configured to be delivered to a graft to reinforce the area surrounding the fenestration and mark the location of the fenestration. In some embodiments, the reinforcement member can be formed as a grommet configured to be delivered to a graft such that the grommet is secured within a fenestration of the graft. The grommet can reinforce the area of the graft surrounding the fenestration and mark the location of the fenestration.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to a direction closer to and away from, respectively, an operator of, for example, a medical device. Thus, for example, the end of the medical device contacting the patient's body would be the distal end of the medical device, while the end opposite the distal end would be the proximal end of the medical device. Similarly, when a device such as an endovascular stent graft is disposed within a portion of the patient, the end of the device closer to the patient's heart would be the proximal end, while the end opposite the proximal end would be the distal end. In other words, the proximal end of such a device can be upstream of the distal end of the device.

As used herein, "reinforced" and variations of "reinforced" (e.g. reinforcing, reinforcement, reinforce) means strengthened or supported such that an edge of a material is prevented from fraying, such that the shape of a portion of a material is maintained, and/or such that engagement and sealing with another material is improved.

The embodiments described herein can be formed or constructed of one or more biocompatible materials. Examples of suitable biocompatible materials include metals, ceramics, or polymers. Examples of suitable metals include pharmaceutical grade stainless steel, gold, titanium, nickel, iron, platinum, tin, chromium, copper, tantalum, and/or alloys thereof. Examples of polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, polyethylene terephthalate (PET), polytetrafluoroethylene (PTFE), and/or blends and copolymers thereof.

The embodiments and methods described herein can be used to form a patient-specific prosthetic device and/or to facilitate the function and/or the integration of the prosthetic device within a portion of a patient. For example, in some embodiments, the devices and/or methods described herein can be used in conjunction with and/or can otherwise include endovascular repair using stent grafts. Although the embodiments are shown and described herein as being used, for example, to facilitate endovascular repair, in other embodiments, any of the devices and/or methods described herein can be used to facilitate treatment of any portion of a patient. For example, the devices and methods described herein can form and/or can facilitate the integration of any suitable implant, prosthesis, device, mechanism, machine, and/or the like within a portion of the body of a patient such as the patient's vascular system, nervous system, muscular-skeletal system, etc. Therefore, while the embodiments are shown and described herein as being used in the endovascular repair of an abdominal aortic aneurysm, they are presented by way of example and are not limited thereto.

Some of the devices and/or methods described herein can be used in minimally invasive treatment techniques such as endovascular repair using stent grafts. Such repair techniques are generally preferred over traditional open surgical repair and often result in reduced morbidity or mortality rates. In some instances, however, the arrangement of the diseased vasculature can result in a need to alter a portion of the stent graft prior to insertion into the body. For example, in an endovascular repair of an abdominal aortic aneurysm, the aneurysm can be situated adjacent to and/or directly distal to normally functioning vessels branching from a portion of the aorta. In order to reline the aneurysm with the stent graft, surgeons often cut openings in the stent graft fabric to accommodate specific branch vessel origins, a process known as "fenestration." Specifically, in treating juxtarenal aneurysms, for instance, the fenestrations or openings of the stent grafts can correspond to a size, shape, and/or relative position of, inter alia, the left and right renal arteries, the superior mesenteric artery (SMA), and/or the celiac artery.

Traditionally, the fenestration process involves measurements based on medical images (such as CT scans) of the vessel origins. For example, in some instances, longitudinal distances of branch vessels can be measured and relative angular locations of the branch vessels can be estimated and/or calculated from a reference point. Based on these measurements and/or calculations, a surgeon or manufacturer can mark and cut the stent fabric of a stent graft to define one or more fenestrations. The fenestrated stent graft can then be positioned within the diseased vasculature (e.g., via an endovascular procedure) and oriented to substantially align the fenestrations with openings of the corresponding branch vessels.

In various embodiments, a fenestration can be created in a prosthetic implant, such as a stent graft, using any suitable method. For example, fenestrations can be created using a fenestration template manufactured using any suitable technologies such as 3-D printing or additive prototyping/manufacturing technologies, subtractive manufacturing techniques, 2-D printing, and the like or a combination thereof. In some embodiments, the fenestration templates are generated for patient-specific anatomy, for example, based on patient specific imagine data. Examples of such fenestration templates and the generation of such fenestration templates are described in U.S. Patent Publication No. 2013/0296998, filed May 1, 2013, entitled "Fenestration Template For Endovascular Repair of Aortic Aneurysms"; U.S. Pat. No. 9,629,686, issued Apr. 25, 2017 and titled "Devices and Methods for Anatomic Mapping for Prosthetic Implants"; and U.S. Pat. No. 9,629,705, issued Apr. 25, 2017 and titled "Devices and Methods for Anatomic Mapping for Prosthetic Implants"; the entire disclosures of which are incorporated herein by reference.

In some embodiments, a fenestration can be created in a stent graft using any suitable method. For example, similarly as described with reference to FIGS. 3-6 below, a number of cuts can be created to segment the graft into a number of triangle or pie slice-shaped flap portions. The flap portions can be pulled or folded into a folded configuration such that the flap portions can be attached to the outer surface of the graft, resulting in the creation of a fenestration. One or more suture threads can be used to attach or reinforce the attachment of the flap portions to the graft in the folded configuration. The suture thread can include a material with radiopaque properties, such as, for example, gold, for visualization of the suture thread using radiographic imaging. Visualization of the suture thread can help a user to identify the location and/or orientation of the graft. Alternatively or in addition to the suture thread, fasteners such as, for example, staples, rivets, micro-rivets, adhesives, and/or welding can be used to secure the flap portions to the graft in the folded configuration. The fasteners can include or be formed of material with radiopaque properties such that the fasteners are visible using radiographic imaging.

In some embodiments, one or more radiopaque beads can be attached to the graft. The beads can be perforated such that each bead can receive a thread for attachment (e.g., sewing) of the beads to the graft. In some embodiments, the beads can be solid. Alternatively or in addition to being sewn to the graft, the beads can be coated with an adhesive material to bond the beads to the graft. For example, the adhesive can be a heat-activated or low melting temperature adhesive or a pressure sensitive adhesive. In some embodiments, the beads themselves can be made from a low melting temperature material that can bond to the graft directly. Any suitable number of beads can be attached to the graft.

In some embodiments, a non-discrete marker can be used to identify the location of and/or reinforce fenestrations in the graft. For example, radiopaque glue can be applied to the graft. In some embodiments, prior to creating a fenestration, the glue can be applied to an area of the graft near a portion intended to be fenestrated. For example, the glue can be applied as a circular band surrounding the area intended for fenestration. After application of the glue, the portion inside of the circular band can be cut to create flap portions as described above. To create the fenestration, the flap portions can be folded into contact with the glue.

In some embodiments, a circular marker, such as a ring or washer-shaped marker, can include a radiopaque material, such as a radiopaque fiber or a radiopaque powder, and be attached to the graft. In some embodiments, the radiopaque fiber or the radiopaque powder can be uniformly distributed throughout the circular marker. Adhesives, such as pressure sensitive adhesives and/or silicone adhesives, can be used to secure the circular marker to the graft. In some embodiments, the circular marker can be secured to the graft via a thermal process. For example, the circular marker can be secured to the graft via an adhesive that can be a heat-activated or a low melting temperature adhesive. Alternatively or additionally, fasteners, such as, for example, staples, rivets, and micro-rivets, can be used to secure the marker to the graft. In addition, as described above, the fasteners can include a material with radiopaque properties such that both the marker and the fasteners are visible using radiographic imaging. Although described as a circular marker, the marker can be any suitable shape, such as ovular, flower-shaped, star-shaped, or rectangular.

In some embodiments, a marker template can be used to aid in positioning radiopaque elements. Similar to the fenestration templates described above, the marker template can be 3-D printed. In some embodiments, the features of a fenestration template and a marker template can be combined to form a combined fenestration and marker template configured to aid in positioning one or more fenestrations and in applying one or more markers.

In some embodiments, a marker template or a combined fenestration and marker template can be formed (e.g., printed) such that markers are incorporated into the template. Additionally or alternatively, the marker template or the combined fenestration and marker template can define apertures configured to receive the markers. For example, FIG. 1 is a schematic illustration of a combined fenestration and marker template 100. As shown in FIG. 1, the template 100 includes a fenestration aperture 110 and a first marking aperture 120A, a second marking aperture 120B, a third marking aperture 120C, and a fourth marking aperture 120D (collectively referred to herein as "marking apertures 120"). The template 100 can be coupled to a graft such that the fenestration aperture 110 is aligned with a desired fenestration location and each of the marking apertures 120 are aligned with a desired graft marker location. A cutting tool (such as any of the cutting tools described herein) can be used to cut out the portions of the graft aligned with the fenestration aperture 110. In some embodiments where a contact cutting tool is used (e.g., a cutting tool with a sharp blade or a cautery device), the cutting tool can be inserted through the fenestration aperture 110 into cutting contact with the graft to cut out the portion of the graft aligned with the fenestration aperture 110. In some embodiments where a non-contact cutting tool is used (e.g., an air knife, a waterjet, or a plasma torch), the cutting tool can be aligned with the fenestration aperture 110 such that the cutting mechanism uses the fenestration aperture 110 as a guide or an outline for cutting the graft. Additionally, a marking tool can be used to apply a radiopaque element (i.e., a marker), such as any of the radiopaque elements described herein, to the portions of the graft aligned with the marking apertures 120. For example, the marking apertures 120 are shaped and sized to allow markers, such as the radiopaque beads described above, to be sewn into the graft through the marking apertures 120 or pop riveted to the graft through the marking apertures 120. The template 100 can then be removed from the graft.

In some embodiments, a fenestration in a graft can be created, before or after the application of any of the reinforcing members described herein, using, for example, a mechanical cutting means (e.g., a sharp blade) or heat application. Additionally, in some embodiments, the cutting tool or another tool can be used to apply heat to seal the edges of the graft. In some embodiments, the cutting tool used to create any of the fenestrations described herein can be harpoon-shaped or U-shaped (i.e., hook-shaped), allowing for the material of the graft to be supported and pulled toward the user during a pull stroke of the user. The cutting tools described herein can be used to create any suitable number, shape, and size of cuts and/or fenestrations.

In some embodiments, one or more markers, such as the radiopaque beads or circular marker described above, can be disposed on an inner surface of the template. A graft can be positioned within the template, and a balloon can be disposed within the graft. The balloon can be inflated such that the balloon presses the graft against the inner surface of the template. In some embodiments, the markers can be automatically transferred from the template to the graft via an adhesive coating on the markers. In some embodiments, the markers can be secured to the graft via a fastener. In some embodiments, one or more markers can be disposed on the outer surface of a template and the template can be positioned within a graft. External pressure can be applied to the graft such that the one or more markers on the outer surface of the template can transfer to the graft via adhesive or the application of fasteners.

In some embodiments, markers (e.g., radiopaque beads) can be secured to a graft, such as an endograft, prior to the graft being cut or fenestrated, to aid in a cutting operation. For example, one or more markers can be sewn into a graft with individual threads. Tension can be maintained on the threads such that the material of the graft can be held taut to aid in cutting the graft. The graft can be cut such that flap portions are created, similarly as described above. The flap portions can be folded and secured to the outer surface of the graft such that a fenestration is defined and reinforced.

In some embodiments, a graft, such as an endograft, can be cut such that flap portions are created, similarly as described above. One or more markers can be placed on or near the flap portions. Each flap portion can be folded such that each flap portion sandwiches at least one of the markers between the flap portion and an outer surface of the graft. The flap portions can then be secured in position using, for example, one or more sutures, adhesive, and/or heat-bonding, thereby securing the radiopaque markers in position.

In some embodiments, a cutting and marking tool can be used to create the fenestration and apply the markers. The cutting and marking tool can be used to create a fenestration similarly to any of the cutting tools described herein. For example, the cutting and marking tool can include a cutting portion and a piercing portion. In some embodiments, the piercing portion can be disposed on an end of the cutting portion. In some embodiments, the piercing portion can be a separate component of the cutting tool than the cutting portion. The piercing portion can be used to create a pilot hole in a graft. For example, the piercing portion can be pushed distally into piercing contact with the graft in an area where a fenestration is desired until the piercing portion has created a pilot hole in the graft. The cutting portion or remainder of the cutting portion can be moved through the pilot hole and into the interior of the graft. Once the cutting portion is on the interior of the graft, the cutting portion can be pulled proximally such that it creates a cut in the graft as it is being pulled proximally and away from the interior of the graft. The cutting and marking tool can also include a marking portion. In some embodiments, the marking portion can deliver a marker to the graft and/or secure a marker to the graft using, for example, suture thread, fasteners, or adhesive.

In some embodiments, a reinforcement member is in the form of a flexible or compliant patch. The flexible or compliant patch can be applied to a graft, such as an endograft, to reinforce and/or mark a fenestration defined by the graft. For example, the patch can be coupled to the area of the intended fenestration to reinforce the fenestration (e.g., prevent fraying) and/or to aid in stiffening the graft for cutting. In some embodiments, the patch can include radiopaque materials. For example, the patch can include radiopaque materials distributed substantially uniformly throughout the patch material. The patch can be formed as a preassembled membrane. In some embodiments, the patch can include one or more radiopaque markers. The radiopaque markers can be embedded in the patch material or secured to the surface of the patch. The patch can be applied to the graft either before or after the fenestration is created. In some embodiments, the patch can be formed as a radiopaque donut-shaped marker. The donut-shaped marker can be flexible and can be formed of a radiopaque membrane material.

The patch can be attached to the graft using any suitable means. In some embodiments, the patch can be sewn to the graft. For example, the patch can be attached via sewing at a number of locations (e.g., four or six). In some implementations, the patch can be attached to the graft via a method in which needles are pre-loaded with sutures and attached to the patch such that all the needles can be activated simultaneously to deliver the sutures through the patch and graft material. In some embodiments, the patch can be secured to the graft with an adhesive, such as a pressure-sensitive adhesive, cyanoacrylate, or a silicone adhesive. The patch can also be secured to the adhesive via heat bonding. In some embodiments, the patch can be heat bonded to the graft. For example, the patch and the graft can both be formed of DACRON® (i.e., polyethylene terephthalate) such that the application of thermal energy creates a DACRON® to DACRON® bond. Alternatively, the patch can be formed of a material with a lower melting point than DACRON® (i.e., such that a temperature differential exists) such that the application of thermal energy allows the patch material to flow within the fibers of the DACRON® material for securement. In some embodiments, the patch can be formed of polyurethane and the graft can be formed of polyethylene terephthalate such that the application of thermal energy can bond the patch to the graft. Additionally, a fenestration in the graft can be created via the application of thermal energy simultaneously, before, or after the bonding of the patch to the graft. In some embodiments, the patch can be secured to the graft via fasteners such as, for example, staples or rivets. In such embodiments, the fasteners can include radiopaque materials.

Figure 2:
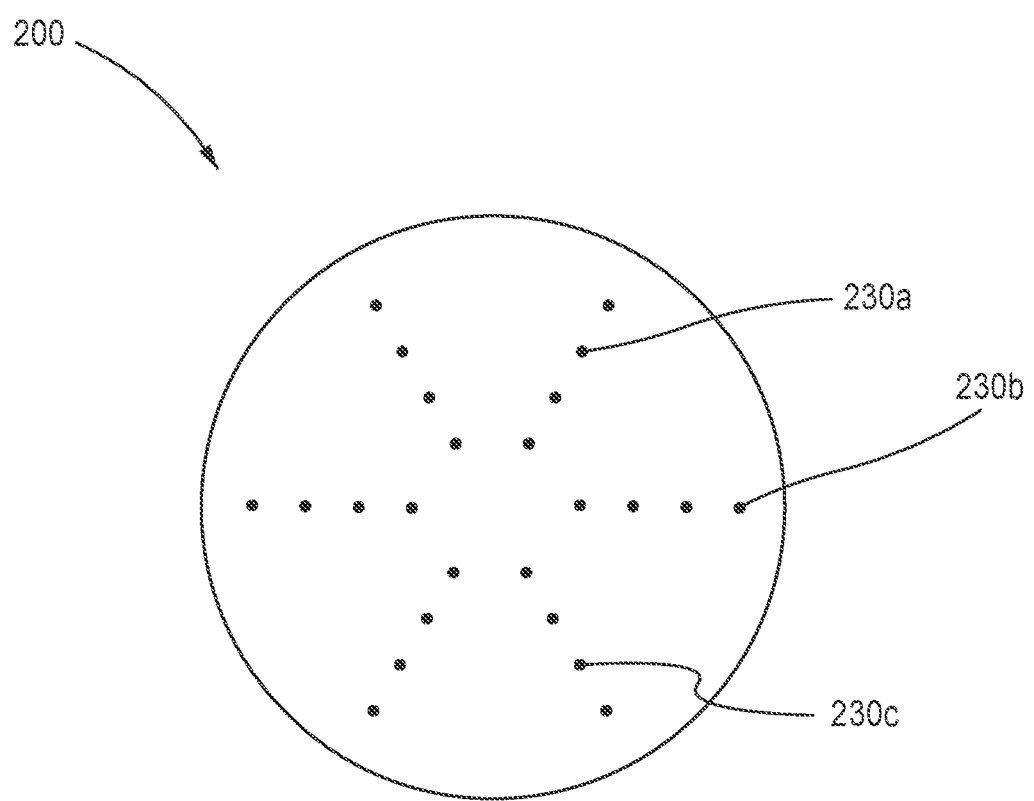
FIG. 2 is a schematic illustration of a patch, according to an embodiment.

The patch can be formed of any suitable material and in any suitable shape or configuration. For example, the patch can be formed of a radiopaque fabric or of any flexible material with a radiopaque material embedded in the flexible material. Additionally or alternatively, in some embodiments, radiopaque markers, such as the radiopaque beads described above, can be embedded in the patch. FIG. 2 is a schematic illustration of a patch 200. As shown in FIG. 2, the patch 200 can be circular. Markers, such as first marker 230A, second marker 230B, and third marker 230C (collectively referred to herein as "markers 230"), can be arranged on the patch 200 in a predetermined pattern, such as a bullseye or a star pattern. In some embodiments, the markers 230 can be used as a cutting template for creating a fenestration in a graft, such as an endograft. In such embodiments, some of the markers 230 may be discarded after cutting the graft during a chard removal step.

In some embodiments, the patch can be formed as a ring. Radiopaque markers can be embedded within the ring. For example, the ring-shaped patch can be formed of silicone or thermoplastic elastomer and molded into a ring shape. Radiopaque markers, such as, for example, tungsten, can be embedded within the outer surface of the ring. In some embodiments, radiopaque markers can be attached to the outer surface of the ring. In some embodiments, the patch can be formed as a circular donut. The circular donut-shaped patch can include a radiopaque material. For example, the circular donut-shaped patch can be formed of foil, radiopaque fiber, or metalized film.

Figure 3:
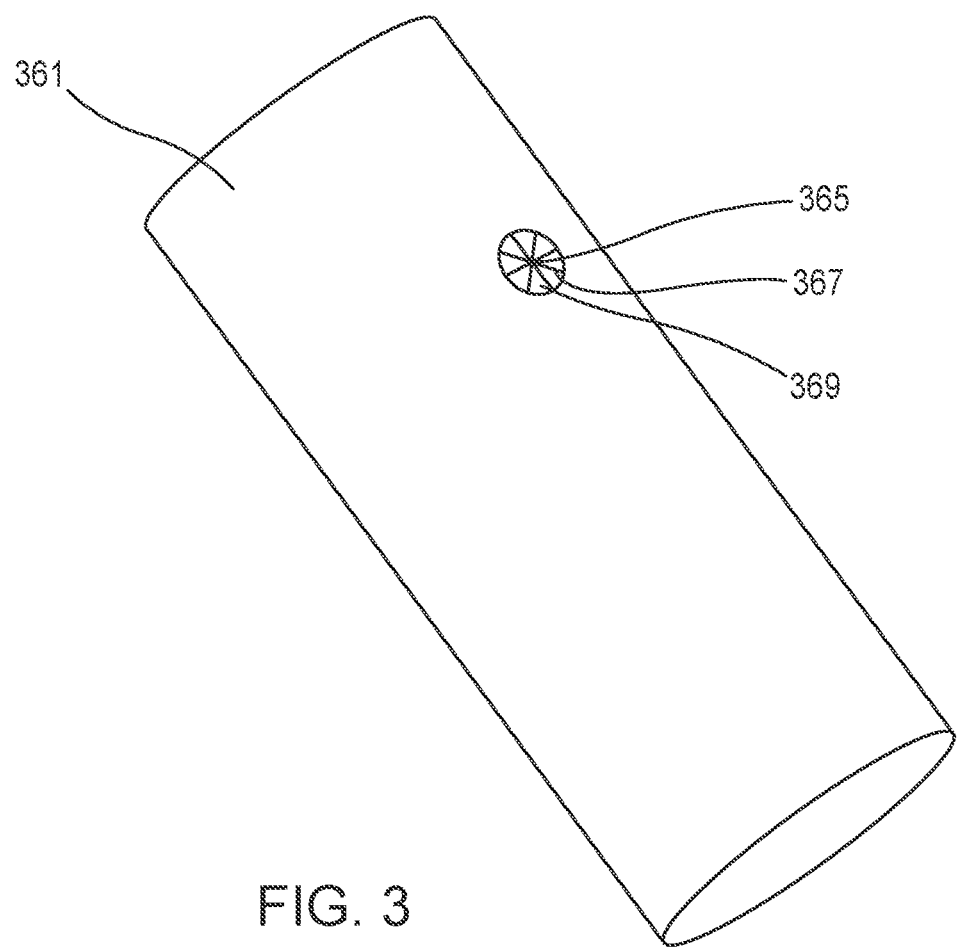
FIG. 3 is a perspective view of a graft in a first configuration, according to an embodiment.

FIGS. 3-6 are various views of an example of a system including a graft 361 and a reinforcing member 340 (also referred to herein as "a reinforcement and marking patch") that can be coupled to the area of the intended fenestration of the graft 361 to aid in stiffening the graft 361 for cutting, to prevent fraying, and/or to mark the location of the fenestrations. The reinforcement and marking patch 340 can be coupled to the graft 361 before or after a cutting operation. For example, FIG. 3 is a perspective view of a graft 361. The graft 361 can be, for example, an endograft. As shown, the graft 361 includes a pilot hole 365, cuts 367, and flap portions 369. Although the graft 361 is shown as having been cut such that it includes eight cuts 367 and eight flap portions 369, the graft 361 can include any suitable number of cuts or flap portions. Additionally, the pilot hole 365 and the cuts 367 can be created through any suitable method described herein.

Figure 4:
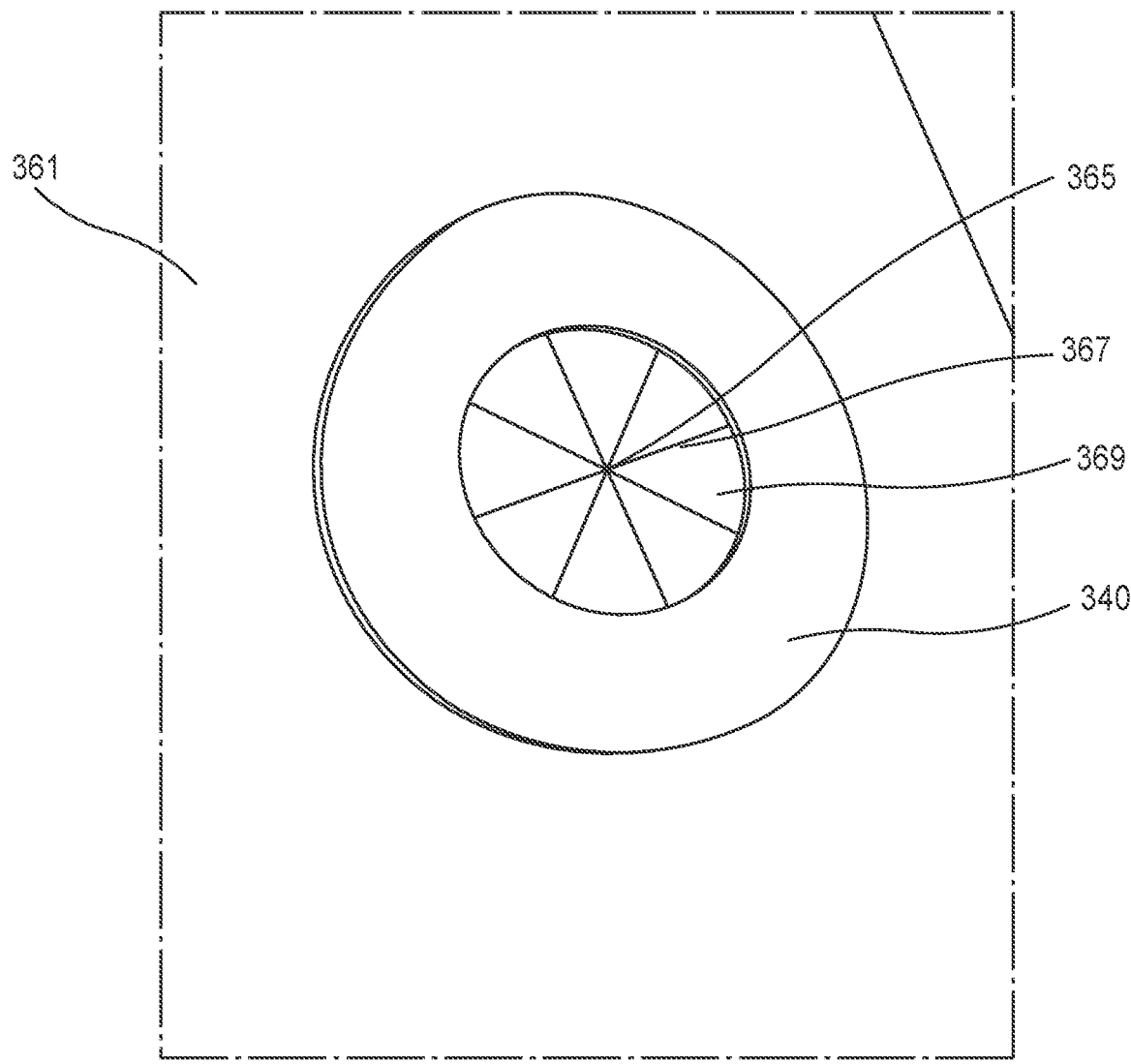
FIG. 4 is an enlarged perspective view of the graft of FIG. 3 in a second configuration, according to an embodiment.

After the flap portions 369 have been created in the side of the graft 361, the reinforcement and marking patch 340 can be coupled to the area surrounding the flap portions 369. For example, FIG. 4 is a close-up view of a portion of the graft 361 with the patch 340 coupled to the graft 361. The patch 340 can be ring or donut-shaped and can be coupled to the graft 361 via any suitable attachment means, such as, for example, adhesive (e.g., pressure sensitive adhesive or silicone adhesive), sutures, or welding (i.e. melting) of the patch 340 to the graft 361. The patch 340 can be arranged relative to the flap portions 369 such that the edges of the cuts 367 are aligned with an internal edge of the patch 340. Although the patch 340 is described as being coupled to the graft 361 after the cuts 367 are created, the patch 340 can be coupled before the creation of the cuts 367 to strengthen the material of the graft 361 in the area of the intended cuts 367. Pre-cut application of the patch 340 can increase the rigidity and/or tautness of the graft 361 in the area of the graft 361 encircled by the reinforcement patch 340 such that the graft 361 is easier to cut. Furthermore, the patch 340 can include radiopaque elements or be formed of a radiopaque material, similar to any of the patches described herein, such that the patch 340 is visible using radiographic imaging.

Figure 5:
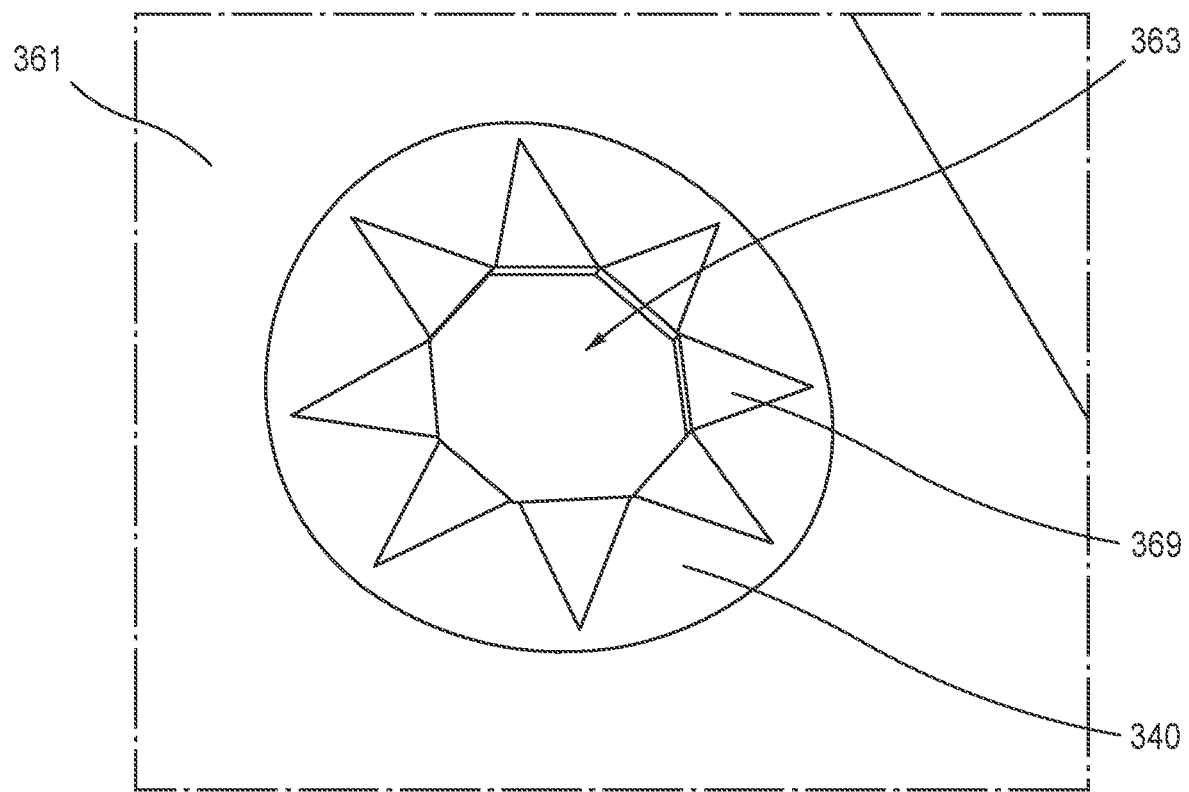
FIG. 5 is an enlarged perspective view of the graft of FIG. 3 in a third configuration, according to an embodiment.

Additionally, the patch 340 can be used to secure the flap portions 369 after the flap portions 369 are pulled proximally away from the interior of the graft 361 and folded toward the outer surface of the graft 361. For example, FIG. 5 is a close-up view of a portion of the graft 361 with the flap portions 369 attached to the patch 340. As shown in FIG. 5, the flap portions 369 can be folded such that the flap portions 369 lie flat against the surface of the patch 340, resulting in fenestration 363. In some embodiments, the patch 340 can be coated in pressure-sensitive adhesive such that the flap portions 369 are secured to the patch 340 after being folded into contact with the patch 340. In some embodiments, fasteners (not shown), such as sutures, staples, rivets, and micro-rivets, can be used to suture the flap portions 369 into a secure relationship with the patch 340 and/or the graft 361. In some embodiments, the pressure-sensitive adhesive and/or fasteners can include a material with radiopaque properties such that the pressure-sensitive adhesive or fasteners are visible using radiographic imaging. In still other embodiments, the flap portions 369 can be bonded via thermal energy (e.g., welded) to the patch 340 such that the flap portions 369 are secured in the position shown in FIG. 5.

Figure 6:
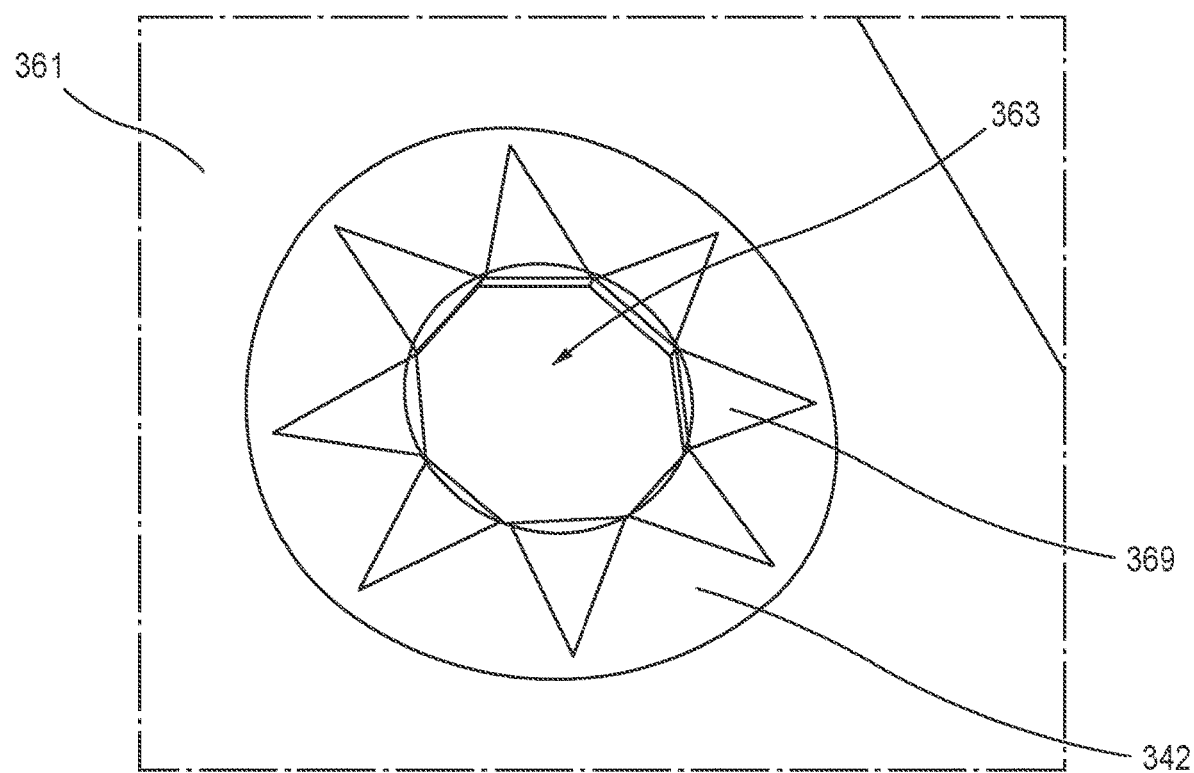
FIG. 6 is an enlarged perspective view of the graft of FIG. 3 in a fourth configuration, according to an embodiment.

Additionally, an optional outer patch can be coupled to the flap portions 369 and the patch 340 to further secure the flap portions 369 in place. For example, FIG. 6 is a close-up view of a portion of the graft 361 with an outer patch 342 shown as being transparent. The outer patch 342 can be coupled (e.g., adhered) to the patch 340 (shown in FIG. 5) and the flap portions 369 such that the flap portions 369 are secured between the patch 340 and the outer patch 342. The outer patch 342 can include an adhesive on the side of the outer patch 342 in contact with the flap portions 369 and the patch 340. In some embodiments, the outer patch 342 can be fastened (i.e., sutured, stapled, or riveted) to the flap portions 369, the patch 340, and/or the graft 361. In some embodiments, the adhesive and/or fasteners can include a material with radiopaque properties such that the adhesive or fasteners are visible using radiographic imaging. In still other embodiments, the outer patch 342 can be bonded via thermal energy (e.g., welded) to the flap portions 369, the patch 340, and/or the graft 361. Furthermore, the outer patch 342 can include radiopaque elements or be formed of a radiopaque material, similar to any of the patches described herein, such that the outer patch 342 is visible using radiographic imaging.

Although not shown, in some embodiments the patch 340 could not be used. Instead, the flap portions 369 can be folded against the outer surface of the graft 361 and the outer patch 342 can be coupled to the graft 361 such that the flap portions 369 are sandwiched between the outer surface of the graft 361 and the outer patch 342. The outer patch 342 can include adhesive on the side in contact with the graft 361 and the flap portions 369 to secure the outer patch 342 and the flap portions 369 in place. In some embodiments, the outer patch 342, the flap portions 369, and the graph 361 can be fastened (e.g., sutured, stapled, or riveted) in position. In some embodiments, the adhesive and/or fasteners can include a material with radiopaque properties such that the adhesive or fasteners are visible using radiographic imaging. In still other embodiments, the outer patch 342, the flap portions 369, and the graph 361 can be secured in position via welding.

Figure 7:
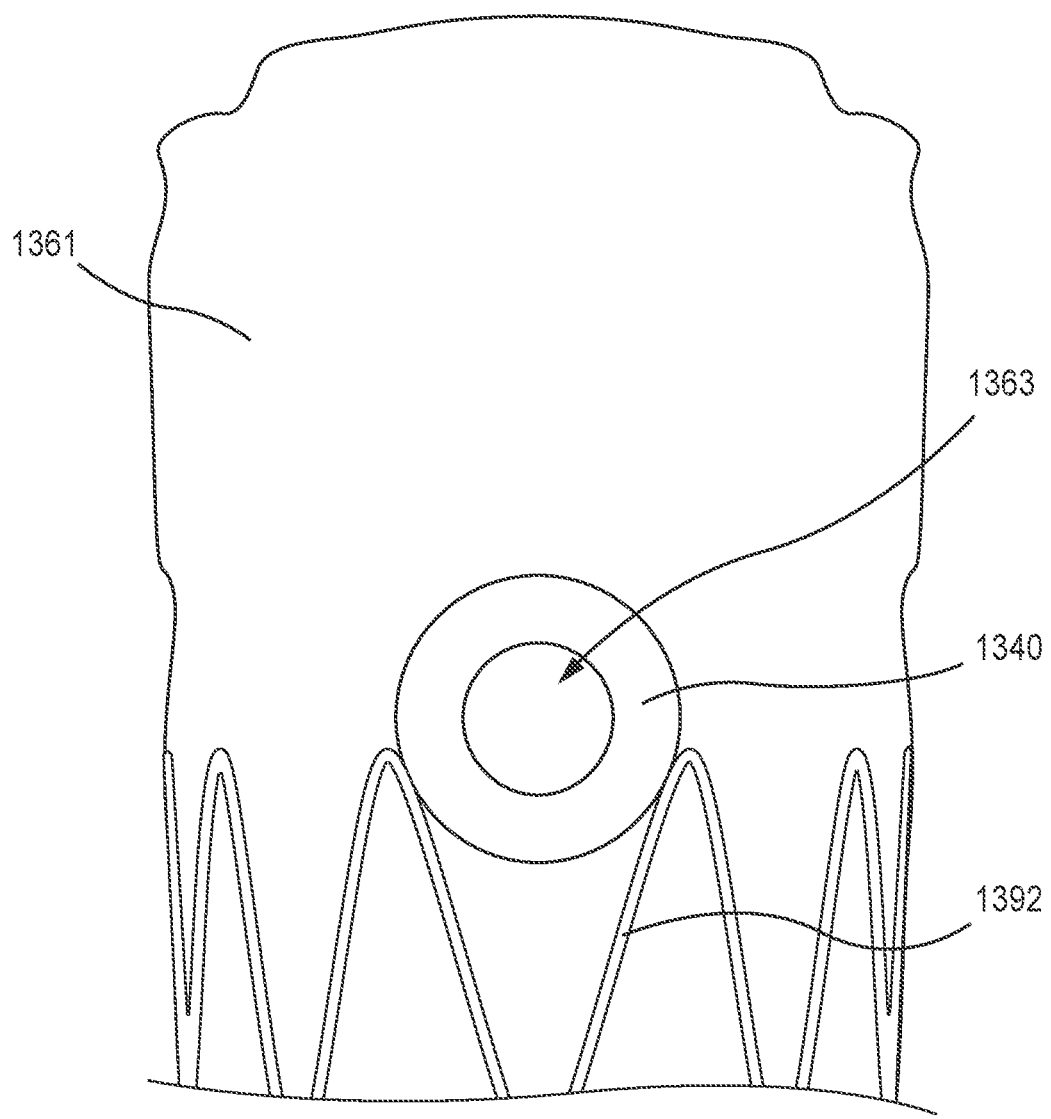
FIG. 7 is a front view of a reinforcing member attached to a graft, according to an embodiment.

In some embodiments, a patch can include uniformly distributed radiopaque material. For example, FIG. 7 shows a front view of a patch 1340 secured to a graft 1361. As shown in FIG. 7, the patch 1340 is substantially circular or donut-shaped (i.e., ring-shaped) and disposed on the graft 1361 such that the patch 1340 is concentric with a fenestration 1363 defined by the graft 1361. The patch 1340 includes radiopaque material such that the patch 1340 can be visible via radiographic imaging. Due to the concentric positioning of the patch 1340 and the fenestration 1363, the location of the fenestration 1363 can be identified via radiographic imaging during placement of the graft 1361 within a patient. For example, the fenestration 1363 can be aligned with a branch artery of a patient while using radiographic imaging to view the patch 1340.

In some embodiments, the patch 1340 can include polyurethane. The radiopaque material within the patch 1340 can be uniformly distributed and can include, for example, tungsten. In some embodiments, the patch 1340 can be disposed over stent struts 1392 of the graft 1361. In some embodiments, the patch 1340 can be disposed such that the patch 1340 does not overlap the stent struts 1392. In some embodiments, the patch 1340 can include cut-outs such that the patch 1340 does not overlap the stent struts 1392. In some embodiments, the patch 1340 can be flexible. The patch 1340 can be secured to the graft 1361 via any suitable coupling method, and specifically via any suitable coupling method described herein. For example, the patch 1340 can be adhesively coupled to the graft 1361. In some embodiments, the patch 1340 can be head bonded to the graft 1361. In some embodiments, the patch 1340 can be sewn or otherwise fastened to the graft 1361. Additionally, the patch 1340 can be applied to the graft 1361 before, simultaneously, or after the fenestration 1363 has been created, similarly as described above with reference to patch 340.

In some embodiments, a reinforcing member can include a first patch and a second patch joined to form a flexible grommet. The flexible grommet can be configured to sandwich one or more markers and/or one or more flap portions of a graft, such as an endograft, created through a fenestration process similarly as described above. In some embodiments, one or more markers can be placed on or near the flap portions. Each flap portion can be folded such that each flap portion sandwiches at least one of the markers between the flap portion and an outer surface of the graft. The first patch can be secured to the outer surface of the graft and the second patch can be secured to the inner surface of the graft such that the flap portions and/or markers are sandwiched between the first patch and the second patch. The first patch and the second patch can be secured to each other and/or the graft using, for example, one or more sutures or threads. Alternatively, the first patch and the second patch can be secured to each other and/or the graft via a sealing process such as heat sealing. In some embodiments, in an assembled configuration, the one or more markers can be disposed between the first patch and a flap portion and/or the graft or between the first patch and the second patch.

Figure 8:
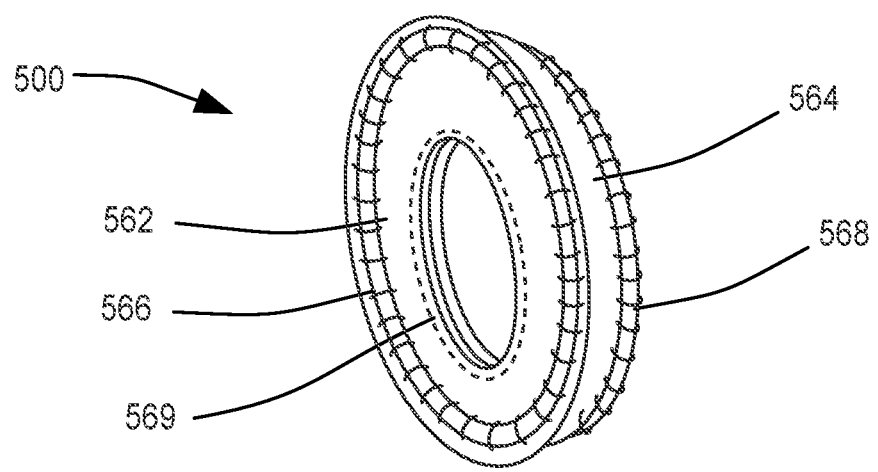
FIG. 8 is a schematic illustration of a perspective view of a reinforcing member, according to an embodiment.

FIG. 8 is a schematic illustration of a perspective view of a reinforcing member 500 (also referred to herein as a "flexible grommet"). The flexible grommet 500 includes a first patch 562 and a second patch 564. The first patch 562 includes a first wire 566. The first wire 566 can be a circular marker wire formed of a radiopaque material. The second patch 564 includes a second wire 568. The second wire 568 can be a circular marker wire formed of radiopaque material. The second wire 568 can be movable between a pre-deployed or deployed, biased expanded configuration and an undeployed, compressed configuration for insertion through a fenestration of a graft. For example, the second wire 568 can be formed of a material having shape-memory properties, such as Nitinol. The second wire 568 can be secured (e.g., sewn or embedded) to the second patch 564 such as, for example, along, near, and/or concentric with the outer edge of the second patch 564 such that the shape and/or position of the second wire 568 can control the shape and/or position of the second patch 564. Said another way, the second wire 568 can be configured to be compressed such that the second wire 568 and the second patch 564 have a smaller diameter in the undeployed configuration than the second wire 568 and the second patch 564 have in the expanded configuration. A surface of the first patch 562 and a surface of the second patch 564 can be heat bonded or joined through any suitable means, such as sewing, along seam 569. In some embodiments, the first wire 566 and the first patch 562 can be the same or similar in structure and/or function to the second wire 568 and the second patch 564 such that either side of the flexible grommet 500 can be inserted through a fenestration in a graft and expand to a deployed configuration such that the flexible grommet 500 is secured within the fenestration and relative to the flexible graft.

Figure 9C:
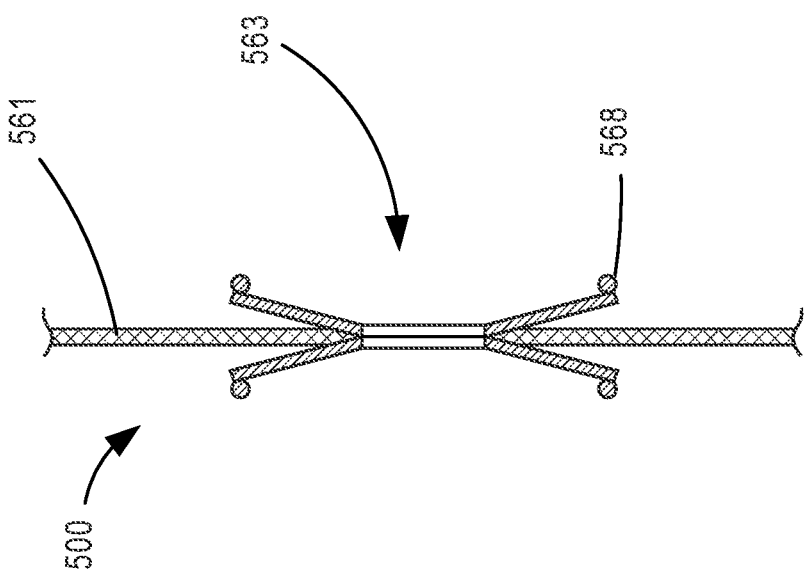
FIG. 9C is a schematic cross-sectional illustration of the reinforcing member of FIG. 8 in a third configuration.
Figure 9B:
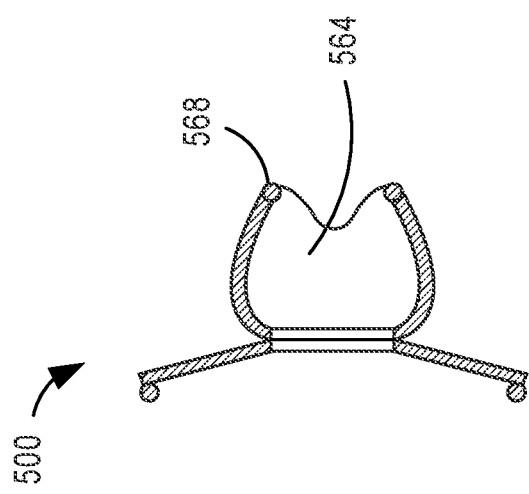
FIG. 9B is a schematic cross-sectional illustration of the reinforcing member of FIG. 8 in a second configuration.
Figure 9A:
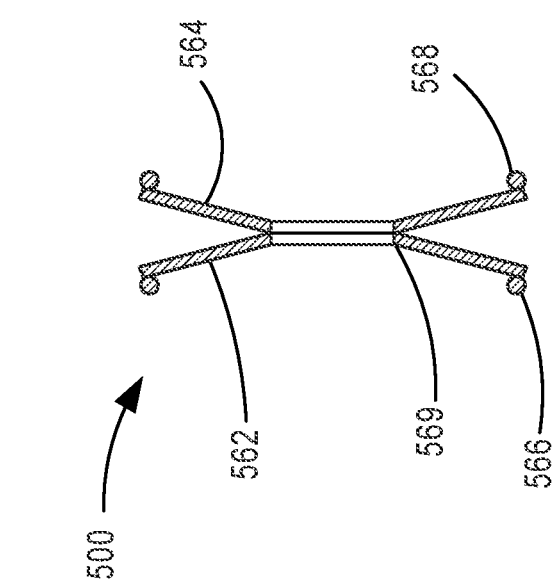
FIG. 9A is a schematic cross-sectional illustration of the reinforcing member of FIG. 8 in a first configuration.

FIGS. 9A-9C are schematic cross-sectional illustrations of the flexible grommet 500 in a pre-deployment configuration, a compressed configuration, and a deployed configuration, respectively. As shown in FIG. 9A, the second wire 568 is in a biased expanded configuration such that the second patch 564 is disc-shaped or donut-shaped (i.e., ring-shaped) prior to insertion of the flexible grommet 500 through a fenestration of a graft. FIG. 9B shows the flexible grommet 500 in a compressed configuration in which the second wire 568 has been compressed or folded such that the second patch 564 can be inserted through a fenestration of a graft. FIG. 9C shows the flexible grommet 500 in a deployed configuration in which the flexible grommet 500 has been inserted through a fenestration 563 in a graft wall 561 and is secured to the graft wall 561. As shown in FIG. 9C, after the second patch 564, including the second wire 568, has been inserted through the fenestration 563, the second wire 568 can be allowed to automatically transition to the deployed configuration due to the second wire 568 having shape-memory properties. As a result of the second wire 568 expanding to the deployed configuration, the flexible grommet 500 is secured to the graft 561. Specifically, the first patch 562 can be positioned on and/or engaged with a first side of the graft 561 and the second patch 564 can be positioned on and/or engaged with a second side of the graft 561. In some embodiments, the first wire 566 and/or the second wire 568 can be configured to expand such that a patch-facing side of the first patch 562 and/or the second patch 564, respectively, partially or fully engages with the surface of the graft 561 to minimize any space between the first patch 562 and/or the second patch 564 with the graft 561. For example, the first wire 566 and/or the second wire 568 can be configured to expand such that the patch-facing side of the first patch 562 and/or the second patch 564 are disposed in contact with the graft 562 around or near at least the outer perimeter of the first patch 562 and/or the second patch 564. Due to the first wire 566 and/or the second wire 568 having radiographic properties and surrounding the fenestration 563, the graft 561 can be positioned within a patient such that the fenestration 563 is aligned with, for example, a branch artery, using radiographic imaging.

Figure 10:
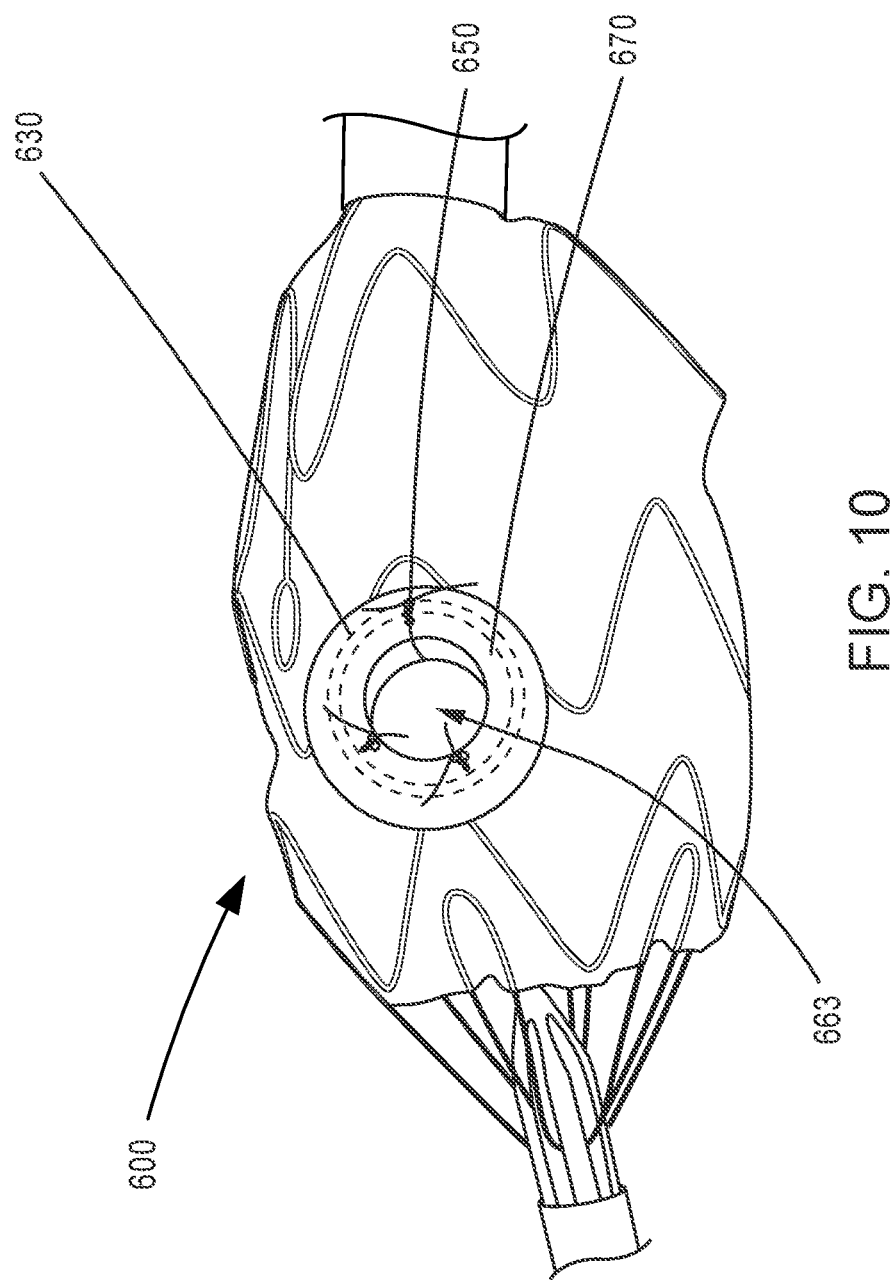
FIG. 10 is a side view of a reinforcing member attached to a graft, according to an embodiment.

In some embodiments, a reinforcing member can be formed by overmolding silicone or another elastomer, such as urethane, over fabric creating a composite material with a radiopaque ring embedded between the layers of silicone and the other elastomer. The reinforcing member can be formed as a flexible patch in a ring or donut-shape. For example, FIG. 10 is a side view of a graft 600 including a reinforcing member 670 (also referred to herein as a "patch"). The patch 670 can include a radiopaque ring or fiber 630 embedded within the patch 670. The patch 670 is secured to the graft 600 via thread 650. As shown, the radiopaque ring or fiber 630 can be arranged such that it is concentric with and/or surrounds a fenestration 663 in the graft 600 such that the location of the fenestration 663 can be identified using radiographic imaging.

Figure 11:
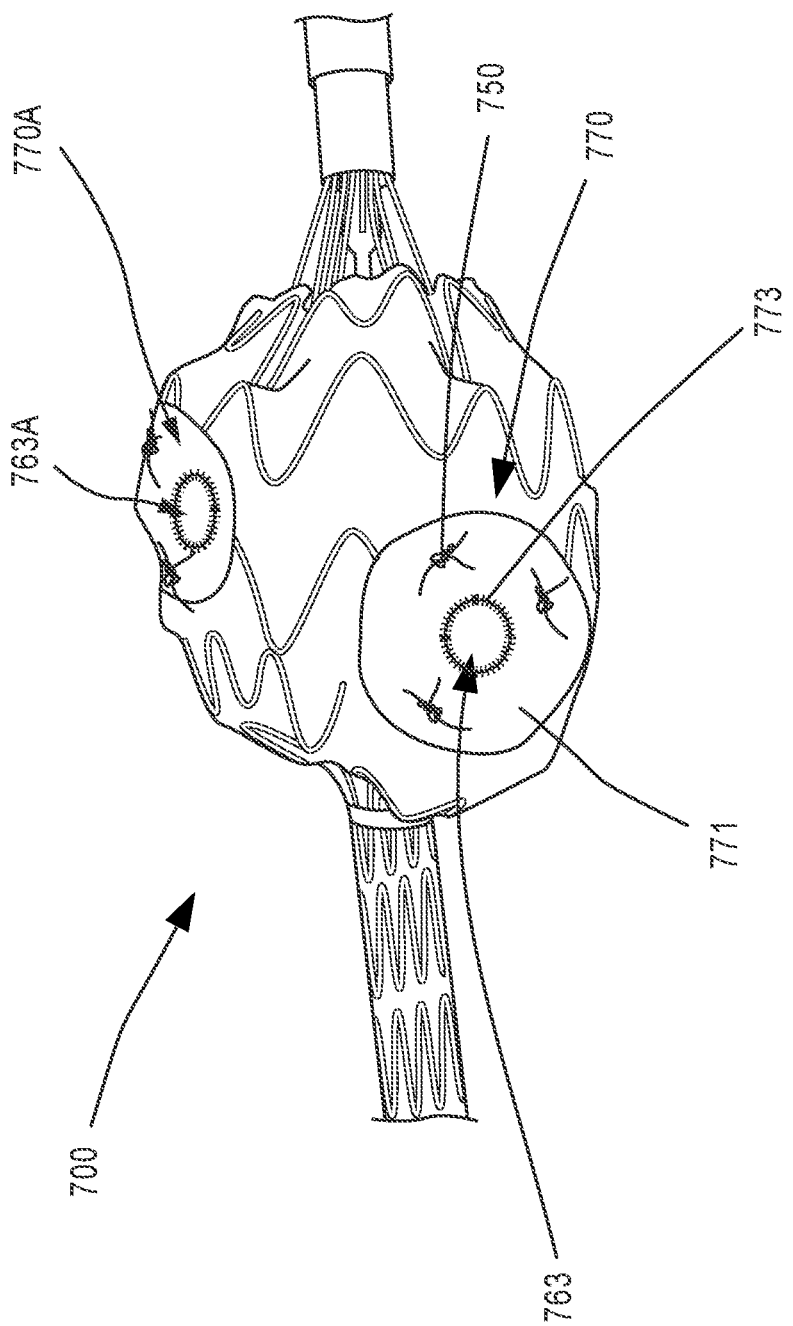
FIG. 11 is a side view of a reinforcing member attached to a graft, according to an embodiment.

In some embodiments, a reinforcing member can be formed as a fabric grommet and encompass a radiopaque ring. FIG. 11 is a side view of a graft 700 including a reinforcing member 770 (also referred to herein as a "flexible grommet" or a "fabric grommet"). As shown in FIG. 11, the flexible grommet 770 can be made of fabric and can include a first ring or donut-shaped fabric portion 771 and a second ring or donut-shaped fabric portion (not shown). The first donut-shaped fabric portion 771 and the second donut-shaped fabric portion can be attached along or near the inner surface of the first donut-shaped fabric portion 771 and the second donut-shaped fabric portion via thread 773. Specifically, the first donut-shaped fabric portion 771 can be disposed on an exterior or first side of the graft 700 and the second donut-shaped fabric portion can be disposed on an interior or second side of the graft 700. A radiopaque ring (not shown) can be disposed between the first donut-shaped fabric portion 771 and the second donut-shaped fabric portion, and can be secured in place relative to the first donut-shaped fabric portion 771, the second donut-shaped fabric portion, and a fenestration 763 of the graft 700 by the thread 773. In some embodiments, the radiopaque ring can be disposed between the first donut-shaped fabric portion 771 and the exterior or first side of the graft 700. In some embodiments, the radiopaque ring can be disposed between the second donut-shaped fabric portion and the interior or second side of the graft 700. Although thread 773 is shown and described, the first donut-shaped fabric portion 771 and the second donut-shaped fabric portion can be attached via any suitable means, such as via adhesive or heat bonding. Additionally, any suitable number of reinforcing members can be attached to the graft 700. For example, as shown in FIG. 11, the graft 700 can include a second flexible grommet 770A secured in surrounding relation to a second fenestration 763A. The second flexible grommet 770A can be the same or similar in structure and/or function to the flexible grommet 770. Thus, both the fenestration 763 and the second fenestration 763A can be identified using radiographic imaging due to the radiographic ring surrounding each fenestration.

Figure 12:
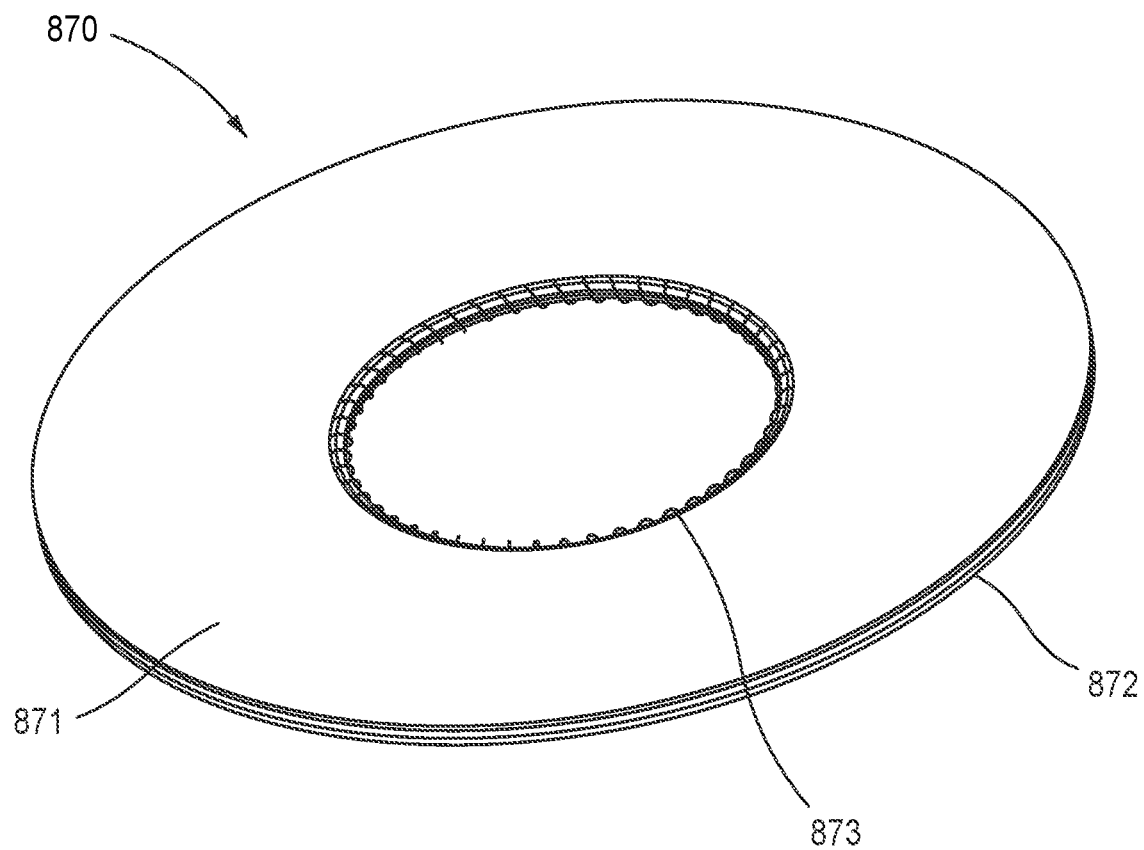
FIG. 12 is a perspective view of a reinforcing member, according to an embodiment.

In some embodiments, a reinforcing member can be formed as a fabric grommet and can include sutures of radiopaque thread. FIG. 12 is a perspective view of a reinforcing member 870 (also referred to herein as a "flexible grommet" or a "fabric grommet"). The flexible grommet 870 can be made of fabric, such as, for example, DACRON®, and can be formed as a first ring or donut-shaped fabric portion 871 and a second ring or donut-shaped fabric portion 872. The first donut-shaped fabric portion 871 and the second donut-shaped fabric portion 872 can be attached along or near the inner surface of the first donut-shaped fabric portion 871 and the second donut-shaped fabric portion 872 via sutures 873. The sutures 873 can be formed of radiopaque thread. Thus, the sutures 873 can be positioned on the flexible grommet 870 such that the sutures can indicate the location of a fenestration of a graft when the flexible grommet 870 is secured within the fenestration of the graft. The flexible grommet 870 can be attached to the graft via, for example, heat sealing or suturing. In some embodiments, the sutures 873 can be used both to secure the first donut-shaped fabric portion 871 to the second donut-shaped fabric portion 872 and to secure both the fabric portions 871, 872 to a graft. In some embodiments, one or both of the first donut-shaped fabric portion 871 and the second donut-shaped fabric portion 872 can also include radiographic materials, such as having a radiographic substance uniformly distributed throughout, such that the fenestration to which the flexible grommet 870 is secured is more easily identifiable using radiographic imaging.

Figure 13:
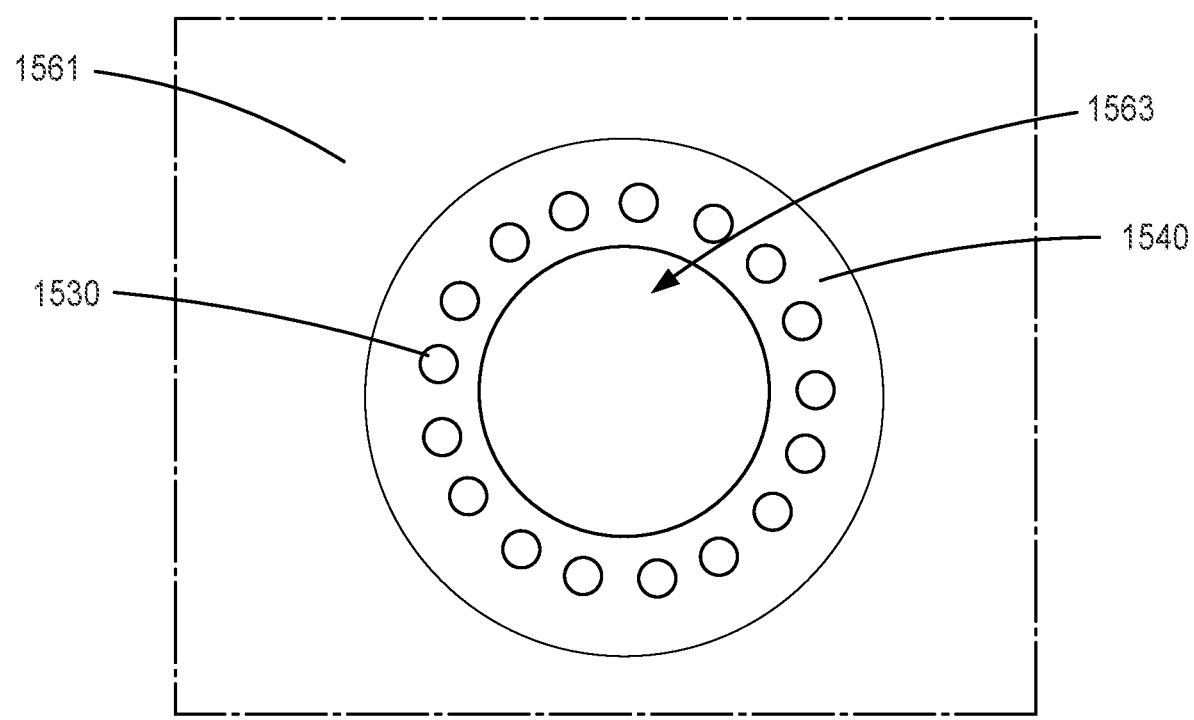
FIG. 13 is a front view of a reinforcing member attached to a graft, according to an embodiment.

In some embodiments, the reinforcing member can be formed as a substrate coupled to the graft such that one or more radiopaque elements are secured relative to a fenestration of the graft. For example, as shown in FIG. 13, a number of discrete radiopaque elements 1530 can be positioned in surrounding relation around a fenestration 1563 in a graft 1561. The substrate 1540 can then be applied (e.g., overmolded) over the discrete radiopaque elements 1530 such that the discrete radiopaque elements 1530 are sandwiched between the substrate 1540 and the graft 1561. Additionally, the substrate 1540 can be applied to the graft 1561 such that the area of the graft 1561 surrounding the fenestration 1563 is reinforced (e.g., fraying is reduced and/or prevented). Although seventeen discrete radiopaque elements 1530 are shown, any suitable number of radiopaque elements 1530 indicating the location of the fenestration 1563 can be used. In some embodiments, the radiopaque elements 1530 can be formed of or coated with, for example, gold, tantalum, and/or platinum. In some embodiments, the substrate 1540 can be formed of or include polyurethane.

Figure 14:
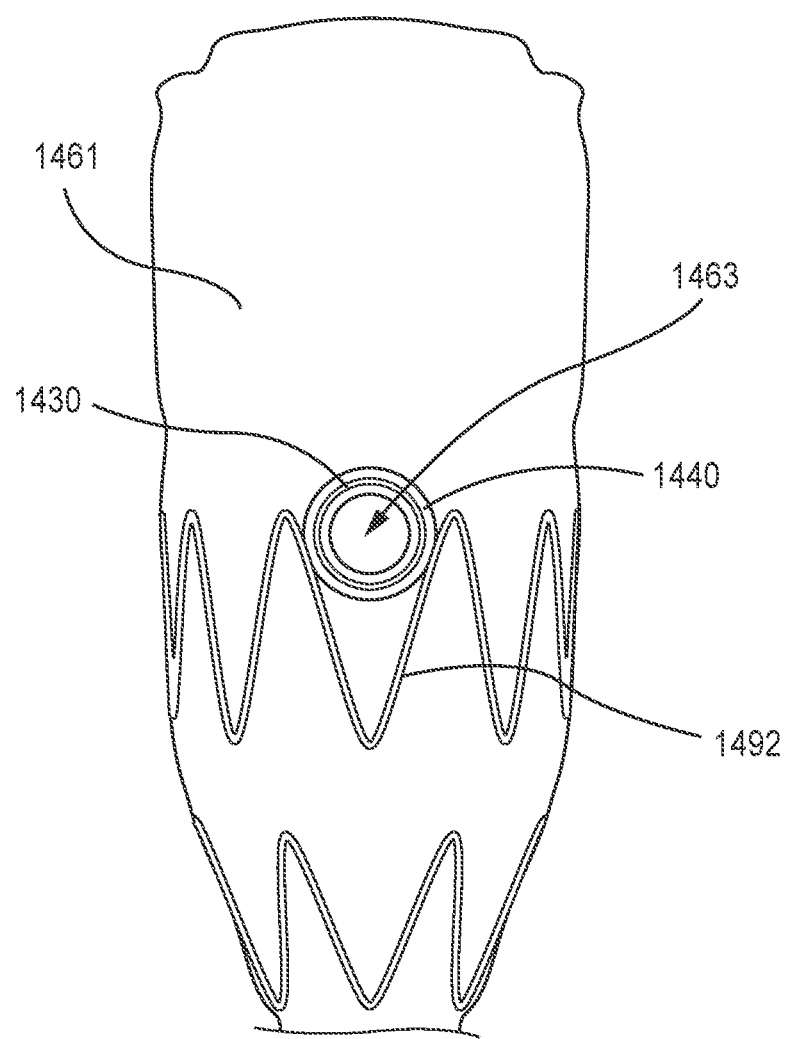
FIG. 14 is a front view of a reinforcing member attached to a graft, according to an embodiment.

In some embodiments, rather than overmolding a substrate onto discrete radiopaque elements and a graft, a substrate can be overmolded onto a radiopaque coil ring and a graft. For example, FIG. 14 shows a radiopaque coil 1430 disposed in surrounding relation (e.g., concentrically disposed) around a fenestration 1463 defined in a graft 1461. A radiopaque substrate 1440 can be overmolded over the radiopaque coil 1430 such that the radiopaque coil 1430 is sandwiched and/or embedded between the substrate 1440 and the graft 1461. In some embodiments, the substrate 1440 can be formed of and/or include polyurethane. Due to the coil 1430 surrounding the fenestration 1463, the location of the fenestration 1463 can be identified via radiographic imaging. In some embodiments the coil 1430 and/or the substrate 1440 can be disposed over stent struts 1492 of the graft 1461. In some embodiments, the coil 1430 and/or the substrate 1440 can be disposed between and/or a distance from the stent struts 1492 such that the coil 1430 and/or the substrate 1440 do not overlap the stent struts 1492. In some embodiments, the substrate 1440 can be formed of polyurethane and the graft 1461 can be formed of polyethylene terephthalate such that the application of thermal energy can bond the substrate 1440 to the graft 1461.

In some embodiments, the reinforcing member can be formed as a grommet formed of overmolded materials such that a radiopaque ring is embedded within the grommet. For example, a radiopaque ring can be embedded between layers of DACRON® and/or silicone via an overmolding process. In some embodiments, a flexible grommet can be formed by overmolding silicone or another elastomer, such as urethane, over fabric with a radiopaque ring embedded between the layers of silicone and the other elastomer.

Figure 15:
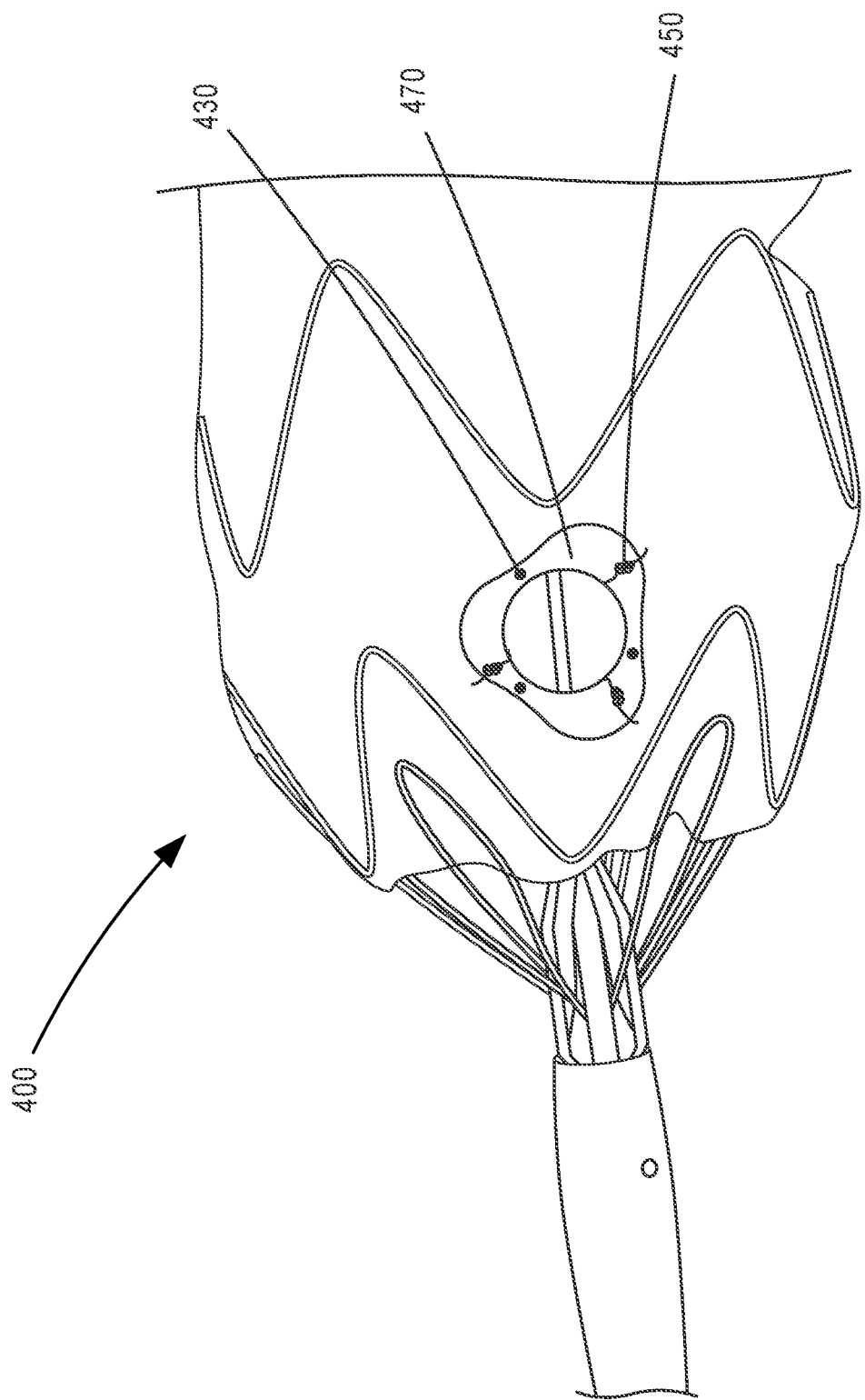
FIG. 15 is a side view of a reinforcing member attached to a graft, according to an embodiment.

In some embodiments, a reinforcing member can be formed as a silicone grommet. For example, FIG. 15 is a side view of a graft 400 including a reinforcing member 470 (also referred to herein as a "leaf grommet") in which a number of leaves are configured to be positioned on the inside of the graft 400 and a number of leaves are configured to be positioned on the outside of the graft 400, thereby sandwiching the graft 400 between the leaves. The leaf grommet 470 includes one or more markers 430 embedded within the leaf grommet 470. Although the one or more markers 430 are shown as discrete markers, in some embodiments the leaf grommet 470 can include a marker 430 formed as a radiopaque ring. The leaf grommet 470 can be secured to the graft 400 via one or more knots including a thread 450 and/or adhesive. Additionally, the leaf grommet 470 can have the same or similar structure and/or function as the leaf grommet 970 described below with reference to FIG. 16.

Figure 16:
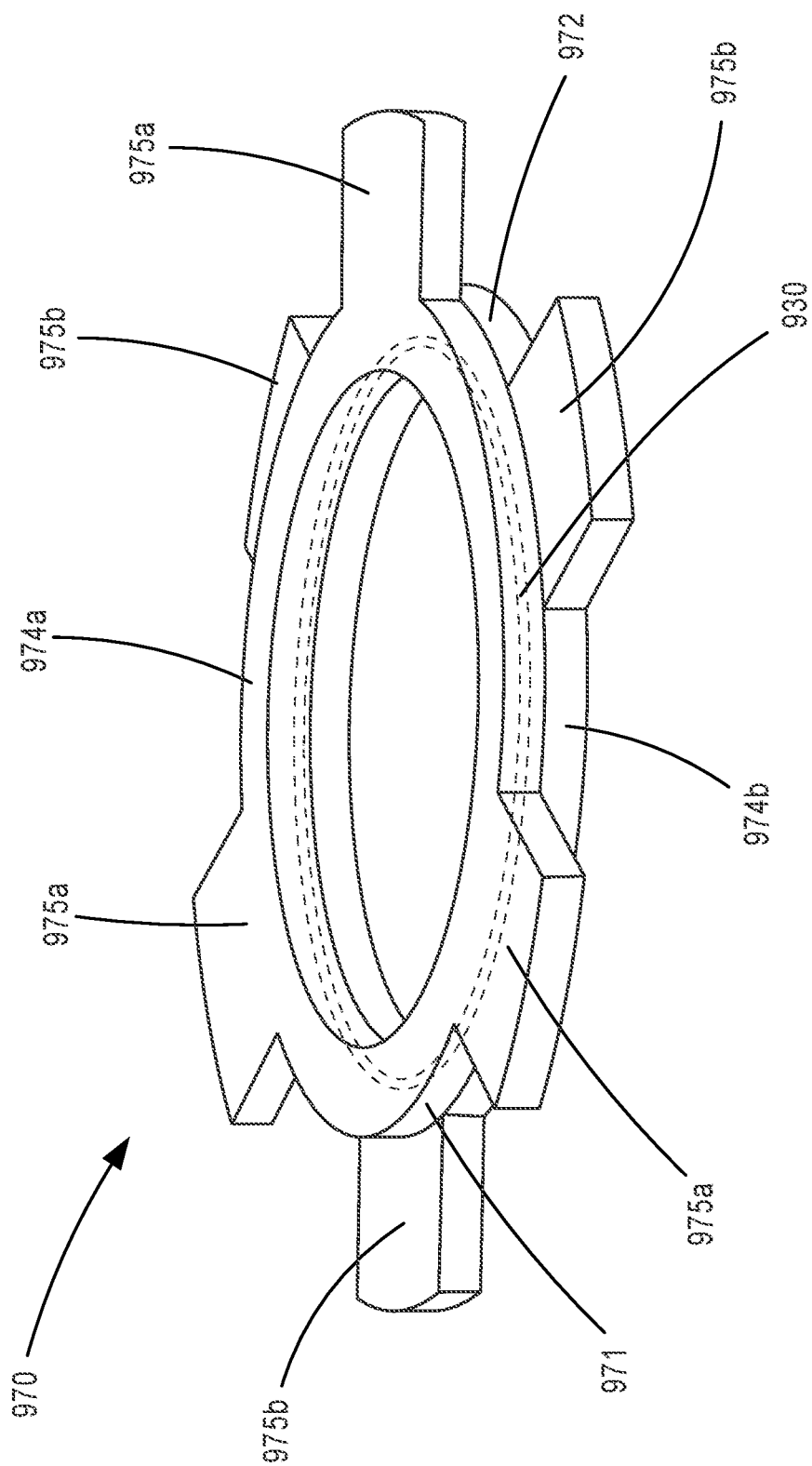
FIG. 16 is a perspective view of a reinforcing member, according to an embodiment.

FIG. 16 is a perspective view of a reinforcing member 970 (also referred to herein as a "grommet"). The grommet 970 can have the same or similar structure and/or function to the leaf grommet 470 described above with reference to FIG. 15. The grommet 970 can include a first portion 971 and a second portion 972. The first portion 971 and the second portion 972 can be formed from silicone. The first portion 971 can include a donut or ring-shaped base 974a and a number of projection portions 975a extending from the base. Similarly, the second portion 972 can include a donut or ring-shaped base 974b and a number of projection portions 975b extending from the base. Although the first portion 971 and the second portion 972 are shown as including three projection portions each, the first portion 971 and the second portion 972 can include any suitable number of projection portions. The projection portions 975a of the first portion 971 and the projection portions 975b of the second portion 972 can be radially offset from each other such that projection portions 975b can be positioned on the inside of a graft and the projection portions 975a can be positioned on the outside of the graft, thereby sandwiching the graft and securing the grommet 970 in position relative to a fenestration of the graft.

The grommet 970 can include a radiopaque ring 930 sandwiched between the first portion 971 and the second portion 972 such that the center of the grommet 970 (and thus, a fenestration of a graft to which the grommet 970 is attached) can be identified using radiographic imaging. In some embodiments, the silicone grommet can include radiopaque thread and/or discrete radiopaque beads, and/or can be formed with radiopaque materials. The grommet 970 can be attached to a graft via sutures, heat bonding, rivets, and/or any other suitable attachment means described herein. In some embodiments, the grommet 970 can reinforce the area of a graft surround a fenestration either before or after the fenestration is created. Although the grommet 970 is described as being formed from silicone, in some embodiments, the grommet can be formed of any other suitable material, such as an elastomer-polyurethane or polyamide. Additionally, although the grommet is shown as being shaped as having a ring-shaped base and projections, the grommet can be any suitable shape. For example, the grommet can be shaped similarly to an O-ring (i.e., having a ring-shaped base but no projections).

Figure 17:
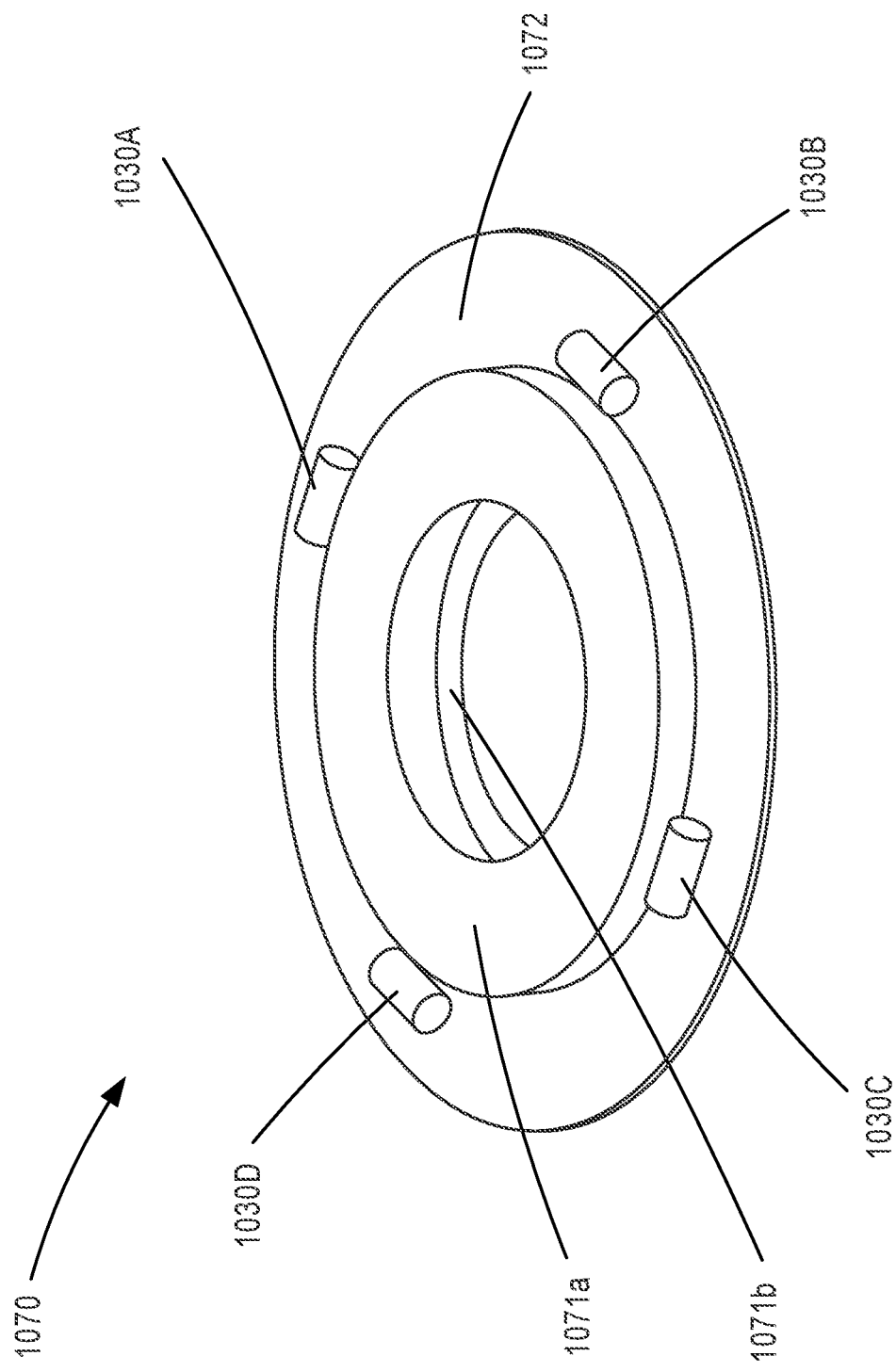
FIG. 17 is a perspective view of a reinforcing member, according to an embodiment.

In some embodiments, a reinforcing member can be formed as a grommet including a combination of fabric, a radiopaque element, and an elastomer material overmolded on the fabric. For example, FIG. 17 is a perspective view of a reinforcing member 1070 (also referred to herein as a "grommet"). The grommet 1070 can include a first portion 1071a, a second portion 1071b, and a third portion 1072. The first portion 1071a and the second portion 1071b can be formed of, for example, silicone. The third portion 1072 can be formed of a fabric, such as, for example, DACRON®. The first portion 1071a, the second portion 1071b, and the third portion 1072 can each be shaped as a circular disc with a central opening. The first portion 1071a and the second portion 1071b can be arranged to sandwich the third portion 1072 such that the openings of the first portion 1071a, the second portion 1071b, and the third portion 1072 are axially aligned. The grommet 1070 can include a first radiopaque element 1030A, a second radiopaque element 1030B, a third radiopaque element 1030C, and a fourth radiopaque element 1030D (collectively referred to herein as "the radiopaque elements 1030"). Although four radiopaque elements 1030 are described and shown in FIG. 17, any suitable number of radiopaque elements 1030 can be included. The radiopaque elements 1030 can include, for example, one or more markers of any suitable shape, such as a ring or bead. The radiopaque elements 1030 can be secured to the third portion 1072 via, for example, an adhesive or suture. In some embodiments, the radiopaque elements 1030 can be embedded between the first portion 1071a and the third portion 1072 and/or between the second portion 1071b and the third portion 1072. For example, the elastomer material of the first portion 1071a and or the second portion 1071b can be overmolded to the fabric of the third portion 1072 such that the radiopaque elements 1030 are embedded between the elastomer and the fabric. The grommet 1070 can be attached to a graft, such as an endograft, via, for example, heat sealing or suturing. The grommet 1070 can be attached to the graft such the first portion 1071A and/or the third portion 1072 is directly secured to the graft and the second portion 1071b is disposed within a fenestration of the graft. The second portion 1071b can be shaped and sized to correspond to the shape and size of the fenestration of the graft such that the shape and size of the fenestration of the graft is maintained and/or to mark the shape and size of the fenestration of the graft. In some embodiments, the first portion 1071a and/or the second portion 1071b can include a radiopaque additive. For example, a radiopaque additive can be uniformly distributed throughout the first portion 1071a and/or the second portion 1071b.

Figure 18:
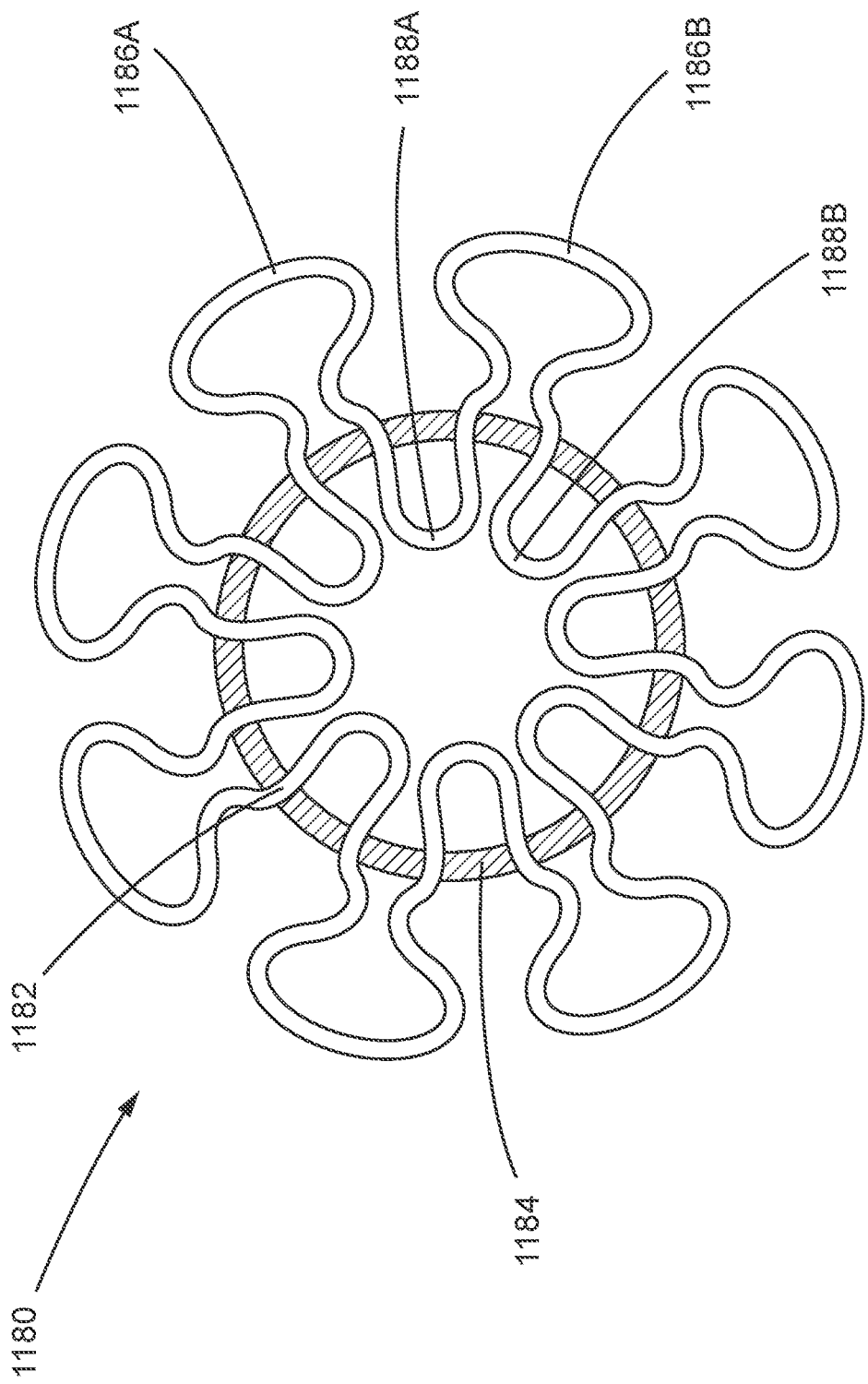
FIG. 18 is a schematic illustration of a reinforcing member, according to an embodiment.

In some embodiments, a reinforcing member can be formed as a crimping apparatus used to mark and/or reinforce a fenestration in a graft. For example, FIG. 18 is a schematic illustration of a reinforcing member 1180 (also referred to herein as a "crimping apparatus"). The crimping apparatus 1180 can include a crimping structure 1182 and a wire or cable 1184. The crimping structure 1182 can be formed from shim stock via, for example, laser cutting. The crimping structure 1182 can be crimpable or foldable around the wire 1184 such that the crimping structure 1182 can be crimped onto an area of a graft (e.g. a graft formed of DACRON® fabric) surrounding a fenestration. The wire 1184 can include a radiopaque material such that the wire 1184 can be visualized using radiographic imaging. The crimping structure 1182 can include outer tabs (e.g., a first outer tab 1186A and a second outer tab 1186B (collectively referred to herein as "outer tabs 1186")) and inner tabs (e.g., a first inner tab 1188A and a second inner tab 1188B (collectively referred to herein as "inner tabs 1188")). The inner tabs 1188 can be folded relative to the outer tabs 1186 through the fenestration upon application of the crimping apparatus to the graft such that the graft is secured between the outer tabs 1186 and the inner tabs 1188 and the wire 1184 surrounds and/or designates the location of the fenestration. The crimping apparatus 1180 can include any suitable number of outer tabs 1186 and inner tabs 1188.

In some embodiments, a reinforcing member can include an outer element and an inner element configured to be positioned on opposite sides of a fenestration in a graft and attached to each other through openings in the graft. The outer element can be formed of, for example, an elastomer material. The outer element can include discrete rigid connection features that can be formed of, for example, plastic. The inner element can be formed as a radiopaque metal ring and can include discrete rigid connection features corresponding to the connection features of the outer element. The connection features of the outer element and the connection features of the inner element can be aligned with the holes in the graft and attached to each other using, for example, ultrasonic welding. In some embodiments, the openings in the graft can be created at the same time the fenestration is created in the graft. In other embodiments, the openings can be created at the time of attachment of the outer element and inner element to the graft.

Figure 19A:
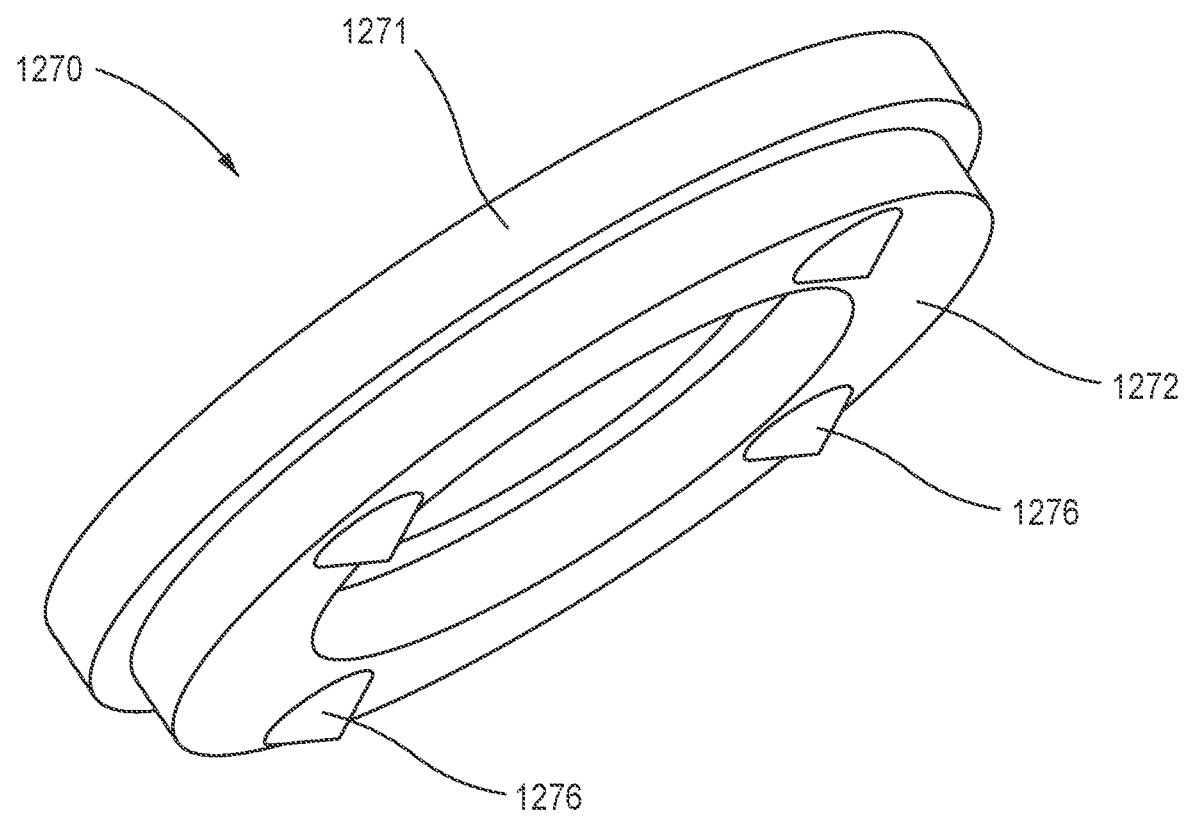
FIG. 19A is a perspective view of a reinforcing member, according to an embodiment.
Figure 19B:
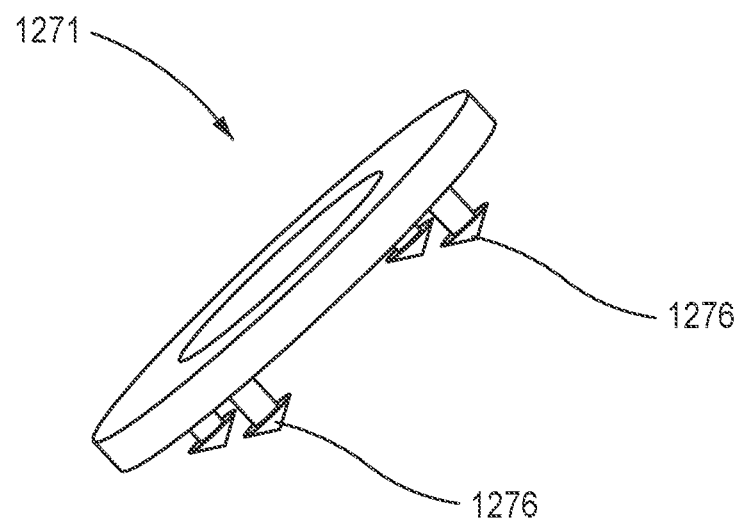
FIG. 19B is a perspective view of an outer element of the reinforcing member of FIG. 19A.
Figure 19C:
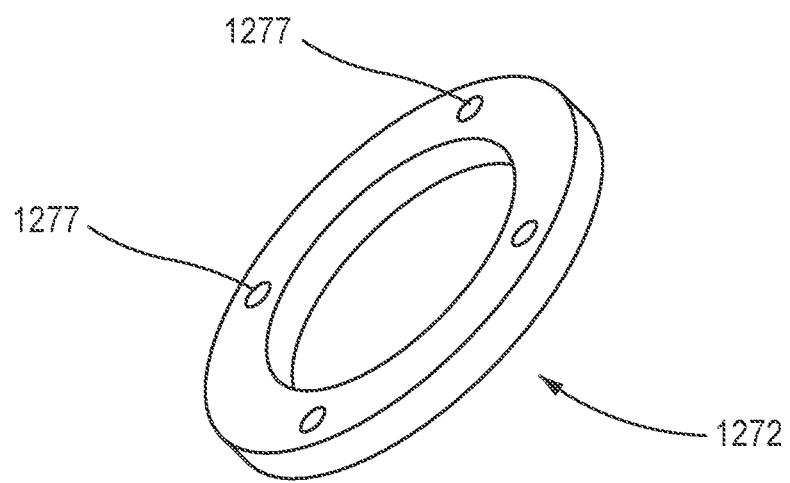
FIG. 19C is a perspective view of an inner element of the reinforcing member of FIG. 19A.
Figure 20:
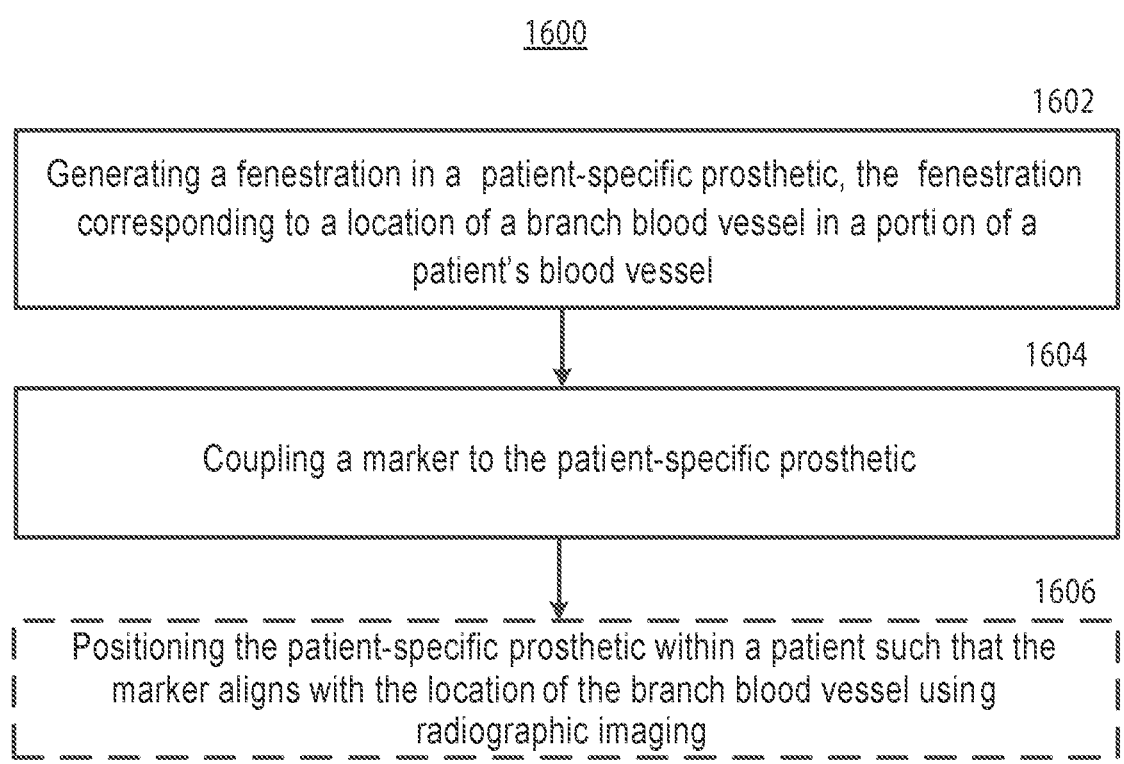
FIG. 20 is a flow chart of a method, according to an embodiment.

In some embodiments, a reinforcing member can include an outer element and an inner element configured to be positioned on opposite sides of a fenestration in a graft and attached to each other through openings in the graft via snap features. For example, FIG. 19A is a perspective view of a reinforcing member 1270 (also referred to herein as a "marking and reinforcing assembly" or an "assembly"). The assembly 1270 includes an outer element 1271 and an inner element 1272. The outer element 1271 includes snap features 1276. Although four snap features 1276 are shown, any suitable number of snap features can be included. The snap features 1276 can include a stem portion and a conical portion. The conical portion can have a larger diameter than the stem portion and can be tapered away from the step portion. As shown in FIG. 19B, which is a perspective view of the outer element 1271, the snap features 1276 can be shaped and sized such that the snap features 1276 can be inserted through an opening in another material, but cannot be withdrawn through the opening once inserted. The outer element 1271 can be formed of, for example, a flexible elastomer material. As shown in FIG. 19C, which is a perspective view of the inner element 1272, the inner element 1272 can define openings 1277 shaped and sized such that the snap features 1276 can pass through the openings 1277 but cannot be withdrawn from the openings 1277 once fully engaged with the inner element 1272. The inner element 1272 can be, for example, a laser cut shim. The inner element 1272 can be more rigid than the outer element 1271. In some embodiments, the openings in the graft can be created at the same time the fenestration is created in the graft. In other embodiments, the openings can be created at the time of attachment of the outer element and inner element to the graft. In some embodiments, the inner element 1272 and/or the outer element 1271 can be formed of a radiopaque material or include discrete radiopaque elements, such as radiopaque beads or thread.

In some embodiments, a method 1600 includes, at 1602, generating a fenestration in a patient-specific prosthetic. The method 1600 can be used with any of the reinforcement members described herein. The fenestration can correspond to a location of a branch blood vessel in a portion of a patient's blood vessel. The method 1600 can further include coupling a marker to the patient-specific prosthetic, at 1604. The marker can include a member configured to be secured to the patient-specific prosthetic such that the patch surrounds the fenestration. The marker can also include at least one radiopaque element configured to indicate the location of the fenestration via radiographic imaging. In some embodiments, the coupling of the marker to the patient-specific prosthetic is performed prior to the generating of the fenestration. In some embodiments, the coupling of the marker to the patient-specific prosthetic is performed after the generating of the fenestration. In some embodiments, the coupling includes applying thermal energy to the marker and the patient-specific prosthetic. In some embodiments, the marker and the patient-specific prosthetic both include polyethylene terephthalate. In some embodiments, the coupling includes overmolding the member onto the at least one radiopaque element and the patient-specific prosthetic. In some embodiments, the coupling of the marker to the patient-specific prosthetic is performed simultaneously to the generating of the fenestration. Optionally, the method 1600 can further include positioning the patient-specific prosthetic within a patient such that the marker aligns with the location of the branch blood vessel using radiographic imaging, at 1606.

While various embodiments of the system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. In addition, the specific configurations of the various components can also be varied. For example, the size and specific shape of the various components can be different than the embodiments shown, while still providing the functions as described herein.

The invention claimed is:

1. An apparatus comprising:
a member configured to be secured to a patient-specific prosthetic such that the member surrounds a fenestration defined by the prosthetic, the fenestration corresponding to a location of a branch blood vessel in a portion of a patient's blood vessel, wherein the member includes a first patch and a second patch, the first patch coupled to the second patch via the fenestration such that the first patch is positioned on a first side of the patient-specific prosthetic and the second patch is positioned on a second side of the patient-specific prosthetic, and
at least one radiopaque element configured to indicate the location of the fenestration via radiographic imaging, wherein the at least one radiopaque element includes a first wire and a second wire, the first wire coupled to the first patch and the second wire coupled to the second patch, the second wire configured to transition between a first configuration having a first diameter and a second configuration having a second diameter, the second diameter being greater than the first diameter, the second wire configured to be compressed such that the second wire and the second patch can be inserted through the fenestration in the first configuration, the second wire configured to be deployed and expanded in the second configuration.

2. The apparatus of claim 1, wherein at least one of the first patch and the second patch is flexible.

3. The apparatus of claim 1, wherein the at least one radiopaque element is embedded in the member.

4. The apparatus of claim 1, wherein the at least one radiopaque element is secured to the surface of the member.

5. The apparatus of claim 1, wherein the at least one radiopaque element includes a circular wire secured to the member.

6. The apparatus of claim 1, wherein the at least one radiopaque element includes radiopaque material uniformly distributed throughout the member.

7. The apparatus of claim 1, wherein the at least one radiopaque element includes two or more discrete radiopaque elements secured to the member.

8. The apparatus of claim 7, wherein the two or more discrete radiopaque elements include at least one of gold, tantalum, and platinum.

9. The apparatus of claim 1, wherein the member includes polyethylene terephthalate.

10. The apparatus of claim 1, wherein the at least one radiopaque element includes at least one of thread, sutures, and adhesive.

11. The apparatus of claim 1, wherein the member is secured to the patient-specific prosthetic via a thermal energy process.

12. The apparatus of claim 11, wherein the thermal energy process activates an adhesive.

13. The apparatus of claims 11, wherein the thermal energy process is operable to thermally bond the member to the patient-specific prosthetic.

14. The apparatus of claim 1, wherein the member is secured to the patient-specific prosthetic via the at least one radiopaque element.

15. The apparatus of claim 1, wherein the member is a ring-shaped patch formed of at least one of a metallic foil, radiopaque fiber, and metalized film.

16. An apparatus, comprising:
a member configured to be secured to a patient-specific prosthetic wherein the member surrounds a fenestration defined by the prosthetic and corresponding to a location of a branch blood vessel in a portion of a patient's blood vessel, the member including a first ring-shaped patch formed of a thermoplastic elastomer, the member further including a second ring-shaped patch, wherein the first ring-shaped patch and the second ring shaped patch are coupled to each other at a fenestration jointly defined by the first ring-shaped member and the second ring-shaped member, the fenestration defined by the first ring-shaped member and the second ring-shaped member corresponding to the fenestration defined by the prosthetic, whereby the member spans the fenestration defined by the prosthetic, the fenestration defined by the first ring-shaped member and the second ring-shaped member thereby corresponding to the location of the branch blood vessel of the patient's blood vessel, and
at least one radiopaque element configured to indicate the location of the fenestration via radiographic imaging, wherein the ring-shaped portion is overmolded over the at least one radiopaque element.

17. The apparatus of claim 16, wherein each of the first patch and the second patch are flexible.

* * * * *